United States Patent
Pastore et al.

(10) Patent No.: US 11,682,111 B2
(45) Date of Patent: Jun. 20, 2023

(54) SEMI-SUPERVISED CLASSIFICATION OF MICROORGANISM

(71) Applicant: International Business Machines Corporation, Armonk, NY (US)

(72) Inventors: Vito Paolo Pastore, Genoa (IT); Simone Bianco, San Francisco, CA (US)

(73) Assignee: International Business Machines Corporation, Armonk, NY (US)

( * ) Notice: Subject to any disclaimer, the term of this patent is extended or adjusted under 35 U.S.C. 154(b) by 594 days.

(21) Appl. No.: 16/823,149

(22) Filed: Mar. 18, 2020

(65) Prior Publication Data

US 2021/0292805 A1    Sep. 23, 2021

(51) Int. Cl.
  *G06T 7/00* (2017.01)
  *G06V 20/69* (2022.01)
  *G06V 10/82* (2022.01)
  *C12Q 1/04* (2006.01)
  *G06F 18/2415* (2023.01)
  *G06V 10/762* (2022.01)

(52) U.S. Cl.
  CPC .............. *G06T 7/0002* (2013.01); *C12Q 1/04* (2013.01); *G06F 18/2415* (2023.01); *G06T 7/0014* (2013.01); *G06V 10/763* (2022.01); *G06V 10/82* (2022.01); *G06V 20/69* (2022.01); *G06V 20/693* (2022.01); *G06V 20/695* (2022.01); *G06V 20/698* (2022.01); *G06T 2207/20084* (2013.01)

(58) Field of Classification Search
None
See application file for complete search history.

(56) References Cited

U.S. PATENT DOCUMENTS

| 6,091,843 A | 7/2000 | Horesh et al. |
| 6,458,584 B1 | 10/2002 | Mirzabekov et al. |

(Continued)

FOREIGN PATENT DOCUMENTS

| CN | 101477630 A | 7/2009 |
| CN | 106372648 A | 2/2017 |

(Continued)

OTHER PUBLICATIONS

Bhuyan et al., Network Anomaly Detection: Methods, Systems and Tools, IEEE Communications Surveys & Tutorials 16(1):303-336 (2014).

(Continued)

*Primary Examiner* — Bernard Krasnic
(74) *Attorney, Agent, or Firm* — Karen Canaan; CanaanLaw, P.C.

(57) ABSTRACT

A system and method that identify and classify unknown microorganisms and/or known microorganisms with anomalies are provided. The system and method comprise processing images of microorganisms from an aquatic environment; extracting features from the processed images; an unsupervised partitioning algorithm for identifying and classifying known microorganisms in the aquatic environment based upon the extracted features; and a supervised classifier neural network that is trained with the unsupervised partitioning algorithm and identifies and classifies unknown microorganisms and/or known microorganisms with anomalies.

15 Claims, 20 Drawing Sheets
(13 of 20 Drawing Sheet(s) Filed in Color)

(56) References Cited

U.S. PATENT DOCUMENTS

| | | | |
|---|---|---|---|
| 8,647,835 B2 | 2/2014 | Walsh et al. | |
| 2016/0371430 A1* | 12/2016 | Mahe | G16B 40/10 |
| 2019/0012430 A1* | 1/2019 | Lu | G16B 40/10 |
| 2021/0080384 A1* | 3/2021 | Lu | H01J 49/0036 |

FOREIGN PATENT DOCUMENTS

| | | |
|---|---|---|
| CN | 109632590 A | 4/2019 |
| JP | 05263411 A | 10/1993 |

OTHER PUBLICATIONS

Biswas et al., High Throughput Analysis of Plankton Morphology and Dynamic, Proceedings SPEI (Standardised Precipitation-Evapotranspiration Index) 2019, vol. 10881, pp. 1-6 (2019).

Zimmerman et al., Stereo in-Line Holographic Digital Microscope, Proceedings SPEI (Standardised Precipitation-Evapotranspiration Index) 2019, vol. 10883 (2019).

Zimmerman & Smith, Lensless Stereo Microscopic Imaging, ACM (Association for Computing Machinery) SIGGRAPH 2007 Emerging Technologies, New York, NY, USA, 2007.

Behrenfeld et al., Biospheric Primary Production During an ENSO Transition, Science 291:2594-2597 (2001).

Blashko et al., Automatic In Situ Identification of Plankton, Proceedings of the Seventh IEEE Workshop on Applications of Computer Vision (WACV/MOTION'05) (2005).

Culverhouse et al., Automatic categorisation of five species of Cymatocylis (Protozoa, Tintinnida) by artificial neural network, Marine Ecology Progress Series 107:273-280 (1994).

Dai et al., ZooplanktoNet: Deep Convolutional Network for Zooplankton Classification, IEEE Oceans 2016, Shanghai, China (2016).

Ho, Random Decision Forests, Proceedings of the Third International Conference on Document Analysis and Recognition 1:278-282 (1995).

Lumini and Nanni, Deep learning and transfer learning features for plankton classification, Ecological Informatics 51:33-43 (2019).

Orenstein and Beijbom, Transfer Learning and Deep Feature Extraction for Planktonic Image Data Sets, 2017 IEEE Winter Conference on Applications of Computer Vision (WACV), pp. 1082-1088 (2017).

Richardson et al., Using continuous plankton recorder data, Progress in Oceanography 68:27-74 (2006).

Romero et al., Unsupervised Deep Feature Extraction for Remote Sensing Image Classification, IEEE Transactions an Geoscience and Remote Sensing 54(3):1349-1362 (2016).

Schmid et al., The LOKI underwater imaging system and an automatic identification model for the detection of zooplankton taxa in the Arctic Ocean, Methods in Oceanography 15-16:129-160 (2016).

Sournia et al., Marine phytoplankton: how many species in the worid ocean?, Journal of Plankton Research 13 (5):1093-1099 (1991).

Yang and Fang, On the accuracy of image normalization by Zernike moments, Image and Vision Computing 28:403-413 (2010).

Grace Period Disclosure: Pastore et al., Annotation-free Learning of Plankton for Classification and Anomaly Detection, bioRxiv (Cold Spring Harbor Laboratory), Nov. 27, 2019 (available at https://www.biorxiv.org/content/10.1101/856815v1).

Grace Period Disclosure: Pastore et al., Establishing the baseline for using plankton as biosensor, bioRxiv (Cold Spring Harbor Laboratory), Oct. 7, 2019 (available at https://www.biorxiv.org/content/10.1101/795203v1).

Benfield et al., RAPID Research on Automated Plankton Identification, Oceanography 20(2):172-187 (2007).

Brieman, Random Forests, Machine Learning 45:5-32 (2001).

Dieleman et al., Exploiting Cyclic Symmetry in Convolutional Neural Networks, available at: arXiv:1602.02660v2 [cs.LG] (Cornell University, 2016).

Fossum et al., Toward adaptive robotic sampling of phytoplankton in the coastal ocean, Science Robotics 4, eaav3041:1-11 (2019).

Gao et al., Random forest algorithm for classification of multiwavelength data, Research in Astronomy and Astrophysics 9(2):220-226 (2009).

Genuer et al., Random Forests: some methodological insights, Rapport de recherche 6729:1-32 (2008).

Gowen et al., The Development of UK Pelagic (Plankton) Indicators and Targets for the MSFD, A Report of a workshop held at AFBI, Belfast (Jun. 2-3, 2011).

Grindstaff et al., Affordable remote monitoring of plant growth in facilities using Raspberry Pi computers, Applications in Plant Sciences 7(8):e11280 (pp. 1-8) (2019).

Haykin, Neural Networks and Machine Learning (Third Edition), Pearson Prentice Hall (New Jersey), 2009.

Hu and Davis, Automatic plankton image recognition with co-occurrence matrices and Support Vector Machine, Marine Ecology and Progress Series 295:21-31 (2005).

Huang and Leng, Analysis of Hu's Moment Invariants on Image Scaling and Rotation, 2nd International Conference on Computer Engineering and Technology (ICCET) V7:476-480 (2010).

Hughes et al., Quantius: Generic, high-fidelity human annotation of scientific images at 105-clicks-per-hour, bioRxiv Gold Spring Harbor Laboratory), Oct. 7, 2019 (available at https://www.biorxiv.org/content/10.1101/164087v1).

McManus and Katz, Molecular and morphological methods for identifying plankton: what makes a successful marriage? Journal of Plankton Research 31(10):1119-1129 (2009).

Reynolds, Gaussian Mixture Models, Gaussian Mixture Models, Li & Jain (eds.) Encyclopedia of Biometrics, Springer, Boston, MA, 2009.

Scholkopf et al., Estimating the Support of a High-Dimensional Distribution, Microsoft Research Technical Report MSR-TR-99-87, Microsoft Research, Redmond, WA, 1999.

Sosik and Olson, Automated taxonomic classification of phytoplankton sampled with imaging-in-flow cytometry, Limnology and Oceanography: Methods 5:204-216 (2007).

Zheng et al., Automatic plankton image classification combining multiple view features via multiple kernel learning, BMC Bioinformatics 18(Supp 16):570 (pp. 1-8) (2017).

* cited by examiner

Arcella Vulgaris
| (%) | In Class | Anomaly |
|---|---|---|
| In Class | 98.6 | 1.4 |
| Anomaly | 0.2 | 99.8 |

Actinospherium Nucleofilum
| (%) | In Class | Anomaly |
|---|---|---|
| In Class | 100.0 | 0.0 |
| Anomaly | 0.1 | 99.9 |

Stentor Ceruleous
| (%) | In Class | Anomaly |
|---|---|---|
| In Class | 99.3 | 0.7 |
| Anomaly | 1.2 | 98.8 |

Didinium Nasutum
| (%) | In Class | Anomaly |
|---|---|---|
| In Class | 100.0 | 0.0 |
| Anomaly | 1.0 | 99.0 |

Euplotes Eurystomus
| (%) | In Class | Anomaly |
|---|---|---|
| In Class | 98.6 | 1.4 |
| Anomaly | 2.0 | 98.0 |

Spirostomum Anbiguum
| (%) | In Class | Anomaly |
|---|---|---|
| In Class | 100.0 | 0.0 |
| Anomaly | 0.7 | 99.3 |

Blaepharisma Americanum
| (%) | In Class | Anomaly |
|---|---|---|
| In Class | 98.6 | 1.4 |
| Anomaly | 2.0 | 98.0 |

Volvox
| (%) | In Class | Anomaly |
|---|---|---|
| In Class | 100.0 | 0.0 |
| Anomaly | 0.0 | 100.0 |

Dilpetus
| (%) | In Class | Anomaly |
|---|---|---|
| In Class | 100.0 | 0.0 |
| Anomaly | 0.4 | 99.6 |

Paramecium Bursaria
| (%) | In Class | Anomaly |
|---|---|---|
| In Class | 92.2 | 8.8 |
| Anomaly | 2.3 | 97.7 |

FIG. 4A

SEMI-SUPERVISED CLASSIFICATION OF MICROORGANISM

STATEMENT REGARDING FEDERALLY SPONSORED RESEARCH OR DEVELOPMENT

This invention was made with Government support under NSF DBI-1548297 awarded by the National Science Foundation. The Government has certain rights in this invention.

STATEMENT REGARDING PRIOR DISCLOSURES BY THE INVENTORS

The following reference is a disclosure under 35 U.S.C. § 102(b)(1)(A): Pastore et al., Annotation-free Learning of Plankton for Classification and Anomaly Detection, bioRxiv (Cold Spring Harbor Laboratory), Nov. 27, 2019.

TECHNICAL FIELD

The present invention relates generally to the classification of microscopic organisms, and more specifically, to the use of learning and neural network-based anomaly detection algorithms to classify microscopic organisms with minimum human supervision.

BACKGROUND OF THE INVENTION

Marine plankton are a class of aquatic microorganisms at the bottom of the food chain. Plankton are composed of both drifters and swimmers, which vary significantly in morphology and behavior. As plankton are at the bottom of the food chain, any disturbance in plankton health propagates up the food chain. The exact number of plankton species is not known, but one estimate of oceanic plankton puts the number between 3444 and 4375. The large number of plankton species makes it is impractical to train a microscope to recognize all of the different classes and types of plankton. The use of artificial intelligence, such as deep learning, to classify plankton has limitations. For example, the use of deep learning to classify plankton requires large datasets, and deep learning solutions for the classification process are computationally expensive.

There remains a need in the art for an efficient and cost-effective way to classify microorganisms, such as plankton.

SUMMARY OF THE INVENTION

The present invention overcomes the need in the art by providing a system that identifies and classifies unknown microorganisms and/or known microorganisms with anomalies with minimal human supervision.

In one aspect, the present invention provides a method comprising: classifying known species from among a population of microorganisms, wherein each of the known species are classified according to a collection of features; developing a neural network for each of the known species; applying each neural network to the population of microorganisms to identify microorganisms with features that are different from the features of the known species; identifying (i) unknown species and/or (ii) known species with anomalies from within the population of microorganisms based upon the features that are different from the features of each of the known species.

In another aspect, the present invention provides a method comprising: classifying known plankton species from among a population of different plankton species, wherein each of the known plankton species are classified according to a collection of features; developing a neural network for each of the known plankton species; applying each neural network to the population of different plankton species to identify plankton species with features that are different from the features of the known plankton species; identifying (i) unknown plankton species and/or (ii) known plankton species with anomalies from within the population of different plankton species based upon the features that are different from the features of the known plankton species.

In a further aspect, the present invention provides a method for use with microorganisms suspended in a fluid, comprising: using an artificial intelligence neural network to classify the most common species of the microorganisms in the fluid; assigning biological labels to the most common species, with expert input; monitoring and identifying anomalies by observing at least one of the following: morphology and behavior of individual microorganisms; and in view of the identified anomalies, making inferences about the environment in which the microorganisms reside.

In another aspect, a DEC (delta enhanced class) detector is used for the monitoring and identifying.

In one embodiment, the present invention comprises a system comprising: an image processor for processing images of microorganisms; a feature extractor for extracting features from the processed images; an unsupervised partitioning module comprising at least one algorithm, wherein the unsupervised partitioning module separates the extracted features into classes and identifies and classifies known microorganisms based upon the extracted feature classes; and a supervised classifier module comprising a neural network, wherein the neural network is trained with the at least one unsupervised partitioning algorithm and the supervised classifier module identifies and classifies (i) unknown microorganisms and/or (ii) known microorganisms with anomalies.

In other aspects and embodiments, the microorganisms are selected from the group consisting of plankton, flagella, amoeba, paramecia, bacteria, protozoans, eukaryotic organelles, prokaryotic organelles, and combinations thereof.

In further aspects and embodiments, the known microorganisms are classified with an unsupervised partitioning algorithm.

In other aspects and embodiments, the collection of features is selected from the group consisting of shape, size, texture, structure, behavior, and combinations thereof.

In other aspects and embodiments, the unsupervised partitioning algorithm is selected from the group consisting of a partition entropy algorithm, a purity algorithm, a random forest algorithm, a clustering algorithm, and combinations thereof.

In further aspects and embodiments, the clustering algorithm is selected from k-Means, Fuzzy k-Means, Gaussian Mixture Model (GMM), and combinations thereof.

In other aspects and embodiments, the neural network is trained with the unsupervised partitioning algorithm.

In further aspects and embodiments, the neural network is selected from the group consisting of an artificial neural network, a convolution neural network, a random forest algorithm, and combinations thereof.

In further aspects and embodiments, the microorganisms are in a fluid and the image processor is a lensless digital microscope.

In other aspects and embodiments, the feature extractor comprises an image processor that extracts microorganism features according to descriptors selected from the group consisting of shape, size, texture, structure, behavior, and combinations thereof.

Additional aspects and/or embodiments of the invention will be provided, without limitation, in the detailed description of the invention that is set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2I are graphical representations of unsupervised clustering results for different plankton species from two separate datasets: a 10-species dataset obtained with a lensless digital microscope (LDM) and a 40-species dataset obtained from Woods Hole Oceanographic Institution (WHOI). FIG. 2A is a graphical rendering of Principal Component Analysis (PCA) results for the LDM dataset showing data distribution into the features space. FIG. 2B shows an assignment of the LDM dataset of FIG. 2A to overlapping clusters using the unsupervised partitioning procedure described herein. FIG. 2C applies the procedure used in FIG. 2A to a 17-species subset from the WHOI dataset. FIG. 2D applies the procedure used in FIG. 2B to the same 17-species subset of the WHOI dataset. FIG. 2E is a box plot showing a distribution of the number of clusters determined by means of a partition entropy algorithm, for random subsets with different numbers of species from the LDM dataset. FIG. 2F is a bar graph showing the class imbalance versus purity for the LDM dataset. FIG. 2H is a graphical rendering of PCA results for the LDM test set showing data distribution into the features space extracted using deep neural networks.

FIG. 2I shows the resulting assignment of the LDM dataset of FIG. 2H to overlapping clusters using the unsupervised partitioning procedure.

FIG. 3A is a multidimensional visualization via Andrews curve; FIG. 3B is a multidimensional visualization via parallel coordinates; FIG. 3C is a receiver operating characteristic (ROC) curve; and FIG. 3D is a confusion matrix.

FIGS. 4A-4E are Delta-Enhanced Class (DEC) detector performances and results. FIG. 4A is a confusion matrix corresponding to 10 neural networks trained on the LMD dataset. FIG. 4B is a bar graph showing the testing accuracy for each of the 10 testing classes of the LDM dataset. FIG. 4C is a bar graph showing the anomaly detection accuracy of the DEC detectors. FIG. 4D is a graph showing the distribution of in silico generated data (obtained using the species *Spirostomum ambiguum*) in the features space. FIG. 4E is a bar graph showing the accuracy of the DEC detectors in revealing an unknown species.

DETAILED DESCRIPTION OF THE INVENTION

Figure 1:
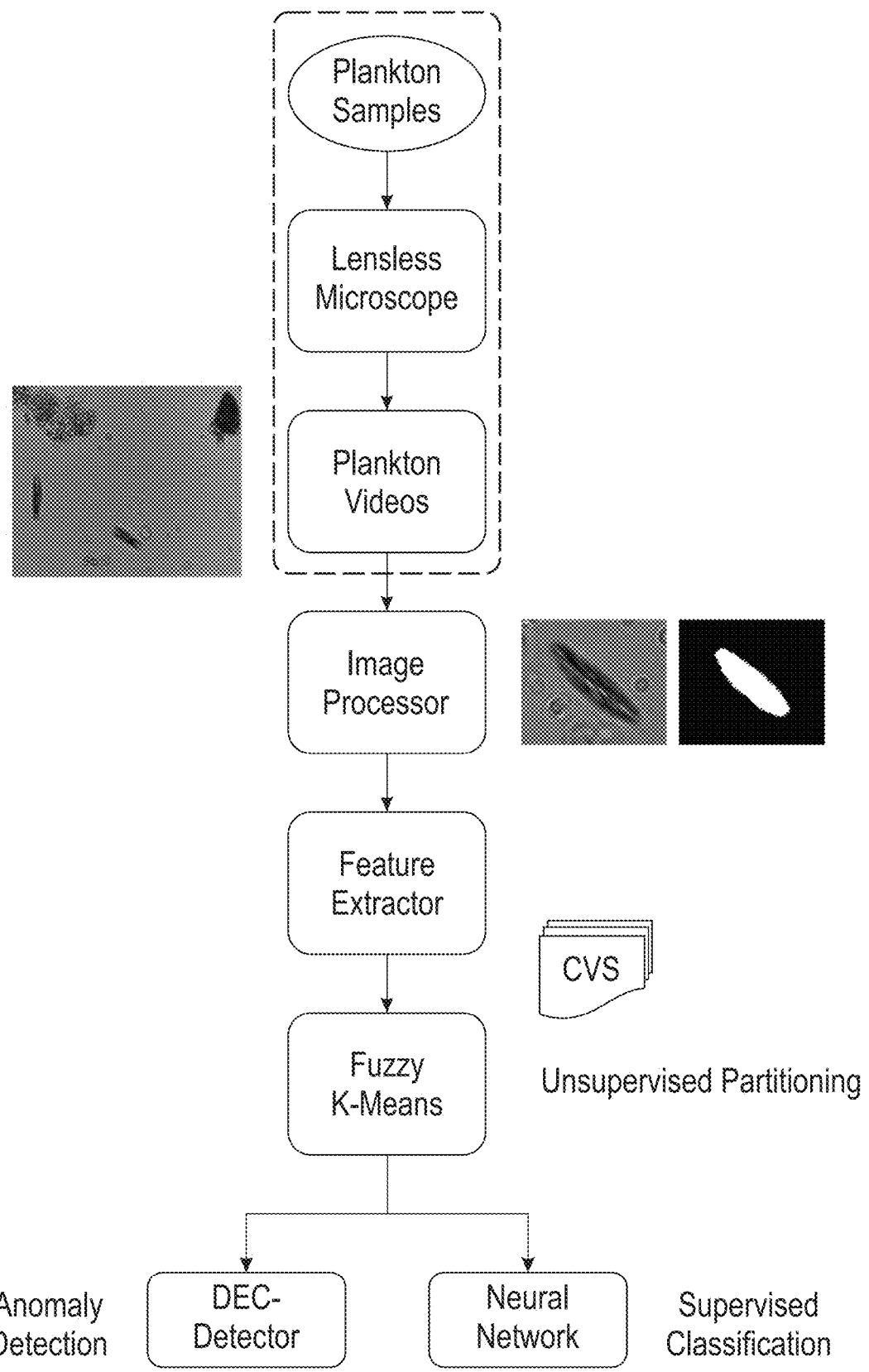
FIG. 1 is a schematic of a plankton classifier system as described herein.

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

The classifier described herein uses plankton as a reference species to describe the function of the classifier for microorganism detection; however, it is to be understood that the classifier is not limited to plankton and may be used to classify other microorganisms, such as for example, flagella, amoeba, paramecia, bacteria, protozoans, eukaryotic organelles, prokaryotic organelles, and combinations thereof. The classifier uses feature vectors extracted from continuously acquired images to reliably characterize plankton species based on morphology and behavior, with minimal human assistance. Using a shallow neural network architecture, the classification system detects anomalies and perturbations that may indicate environmental changes and/or dangers that may affect the species populations. Training and testing, which can be executed in real-time, require low computational resources. Using the computed differences of a training set, the classifier is able to detect if a plankton sample belongs to a known class (i.e., a species seen in the training set) or if it is an anomaly (i.e., a species with some differences from the training set) or an unknown species (i.e., a species not seen in the training set). The classifier is considered semi-supervised because it includes unsupervised and supervised modules.

As used herein, the term "plankter" is used to refer to a single plankton microorganism.

As used herein, the term "morphology" is used to refer to the shape, size, texture, and structure of a microorganism.

As used herein, the term "neural network" is used to refer to a non-linear artificial intelligence system where applications (i.e., natural artificial neurons or nodes) are trained via datasets. The neural network includes all neural networks including artificial neural networks (ANNs), convolutional neural networks (CNNs), and random forest (RF) algorithms. ANNs are interconnected natural and/or artificial processing units (called "neurons") for information processing based on connections between the individual neurons. The network for an ANN is shallow, providing an efficient feature selection process. CNNs are neural networks that are used to analyze visual imagery by using convolution instead of matrix multiplication in at least one of the layers of the neural network. As is known to those of skill in the art, convolution is a mathematical operation on two functions (e.g., x and y) that produces a third function (e.g., z) expressing how the shape of one is modified by the other. RF is an ensemble learning method used for classification and regression tasks. RF uses decision trees to separate training step samples into correct classes.

As used herein, the term "Delta Enhanced Detector" and/or "DEC" is used to refer to the neural network used in the classifier described herein. The DEC identifies and classifies known microorganisms with anomalies and/or unknown microorganism.

FIG. 1 is a schematic of the classifier system, which includes four modules: an image processor, a feature extractor, an unsupervised partitioning module, and a supervised classifier. The "CSV" in FIG. 1 refers to a comma separated value, which is a method known in the art for entering data into an artificial intelligence system. The CSV in FIG. 1 refers to training data that are entered into the system.

Image Processing.

The first step in the application of the classifier system is data acquisition, which includes images of plankton samples. Example 1 describes an imaging process for obtaining plankton videos. As described therein, a collection of videos lasting for 10 minutes and containing 10 freshwater plankton species were imaged with an LDM (lensless digital microscope), which is a microscope designed for in situ data collection. Using a customized algorithm, the image processor examined each frame of video and generated cropped images of each plankter. The dataset of the 10 plankton species obtained with the LDM are referred to herein as "the LDM dataset." While the plankton sample images in Example 1 were obtained with an LDM, it is to be understood that images of plankton, or other microorganisms, may be obtained through other means.

Feature Extraction.

The feature extractor examines each plankter image and generates a collection of features. A sample is considered an anomaly with respect to a class if the extracted features are significantly different from the class average. Example 2 describes extraction of 131 features from the LDM dataset.

Unsupervised Partitioning.

The unsupervised partitioning module clusters samples by features into classes. To obtain the number of classes from a dataset, a partition entropy (PE) algorithm is used. The PE algorithm used herein is represented by Formula (1):

$$PE = -\frac{1}{N}\sum_{i=1}^{N}\sum_{j=1}^{K}u_{ij}*\log(u_{ij}), \quad (1)$$

where the PE coefficient is computed for every j in [0, K] and takes values in the range [0, log(K)], N is the total number of clustering samples, $u_{ij}$ is the degree of membership (i.e., the probability of sample i belonging to cluster j), $$u_{ij}\mu_{ij} \in [0, 1], \text{ and } \sum_{j=1}^{K}u_{ij} = 1.$$

The estimated number of clusters is assigned to the index j* corresponding to the maximum PE value, PE(j*). The lower the PE(j*), the higher the uncertainty of the clustering.

The performance of the PE algorithm was tested on random plankton images (ranging from 3 to 10 plankton species) extracted from the 10-species LDM dataset and a separate dataset of 40 plankton species obtained from WHOI (Woods Hole Oceanographic Institute, Woods Hole, Mass., USA), referred to herein as "the WHOI dataset." WHOI maintains a public dataset that includes millions of still monochromatic images of microscopic marine plankton, captured with an optical Imaging FlowCytobot (IFCB) (McLane Research Laboratories, Inc., East Falmouth, Mass., USA), which is an in situ automated submersible imaging flow cytometer that generates images of particles in flow taken from the aquatic environment. As described in Example 1, the LDM dataset is composed of 500 training samples for each of the plankton species and the WHOI dataset has 140 training samples for each plankton species.

FIGS. 2A-2F show the unsupervised clustering results for the 10-species LDM dataset and a 17-species subset of the WHOI dataset.

Figure 2A:
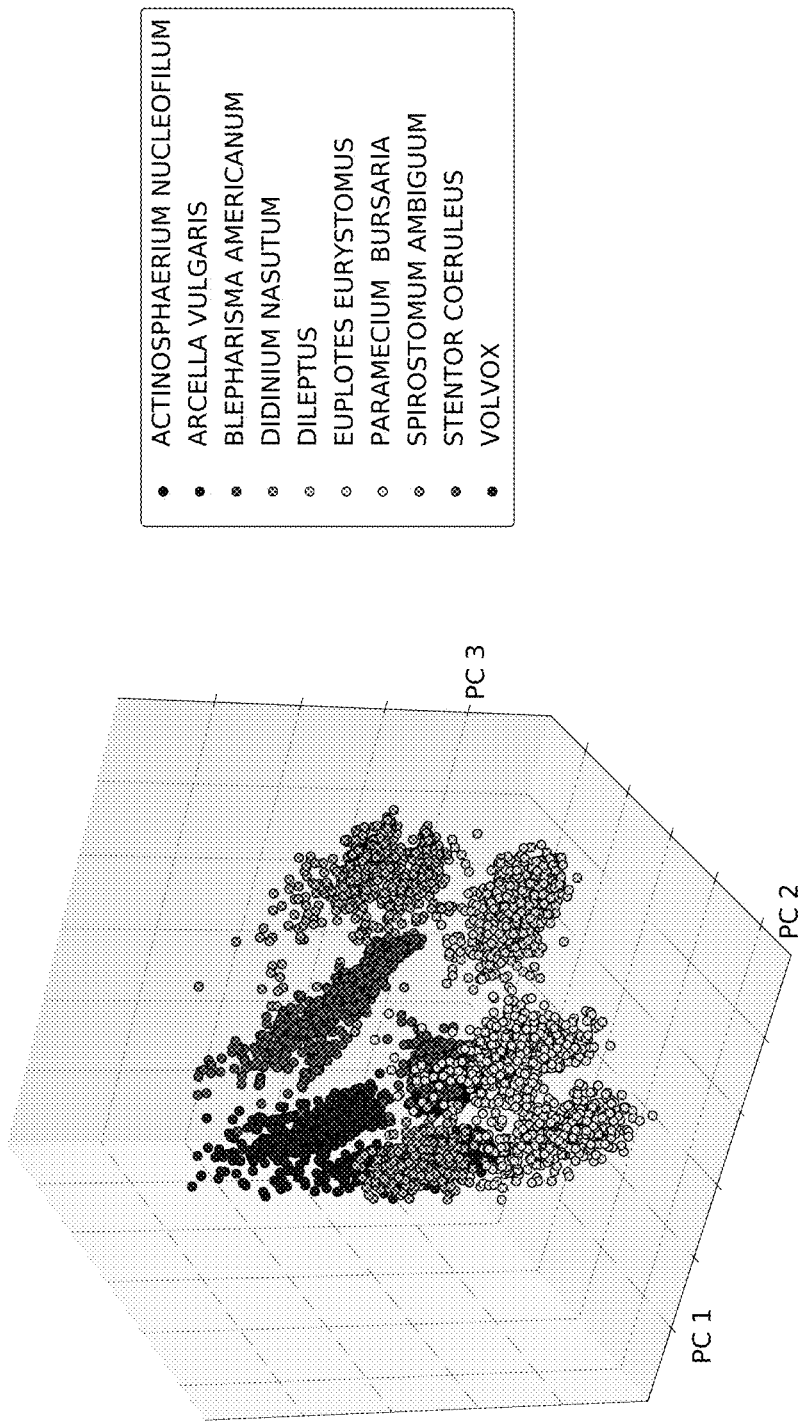
Figure 2B:
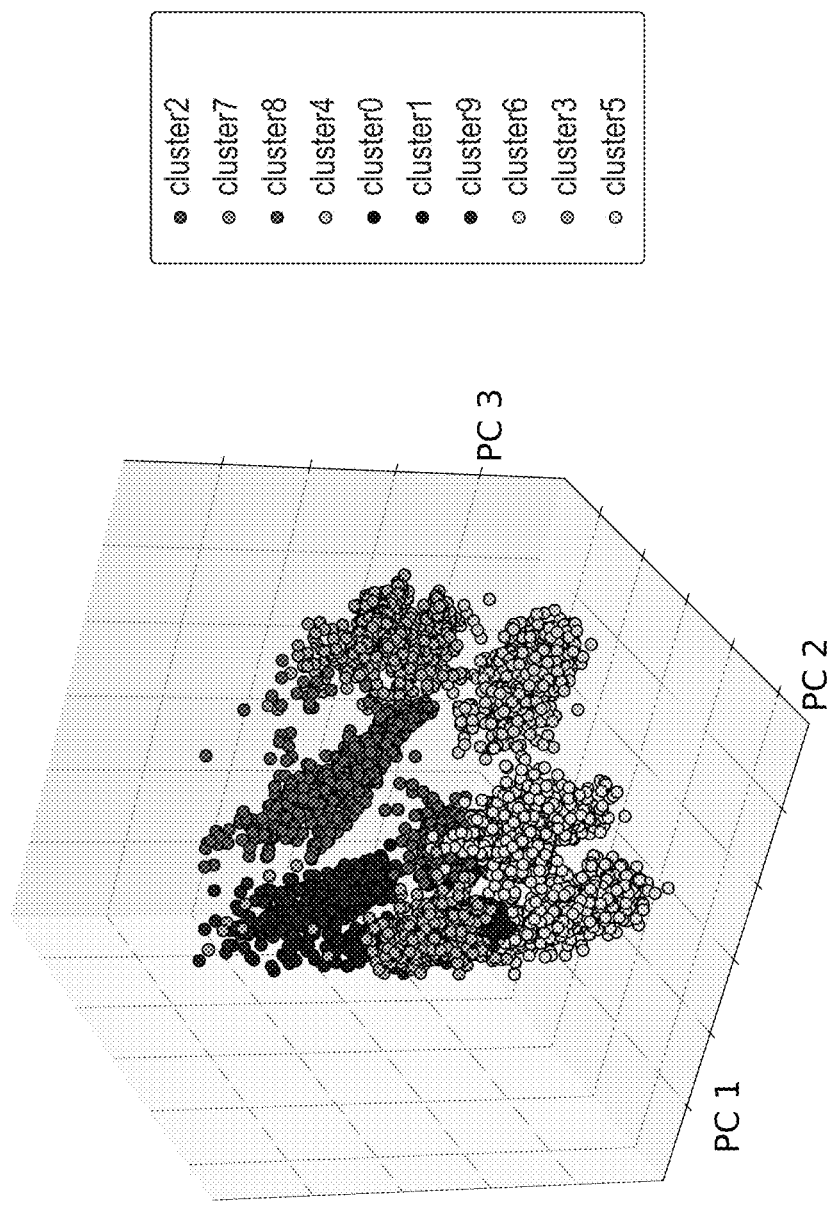
Figure 2C:
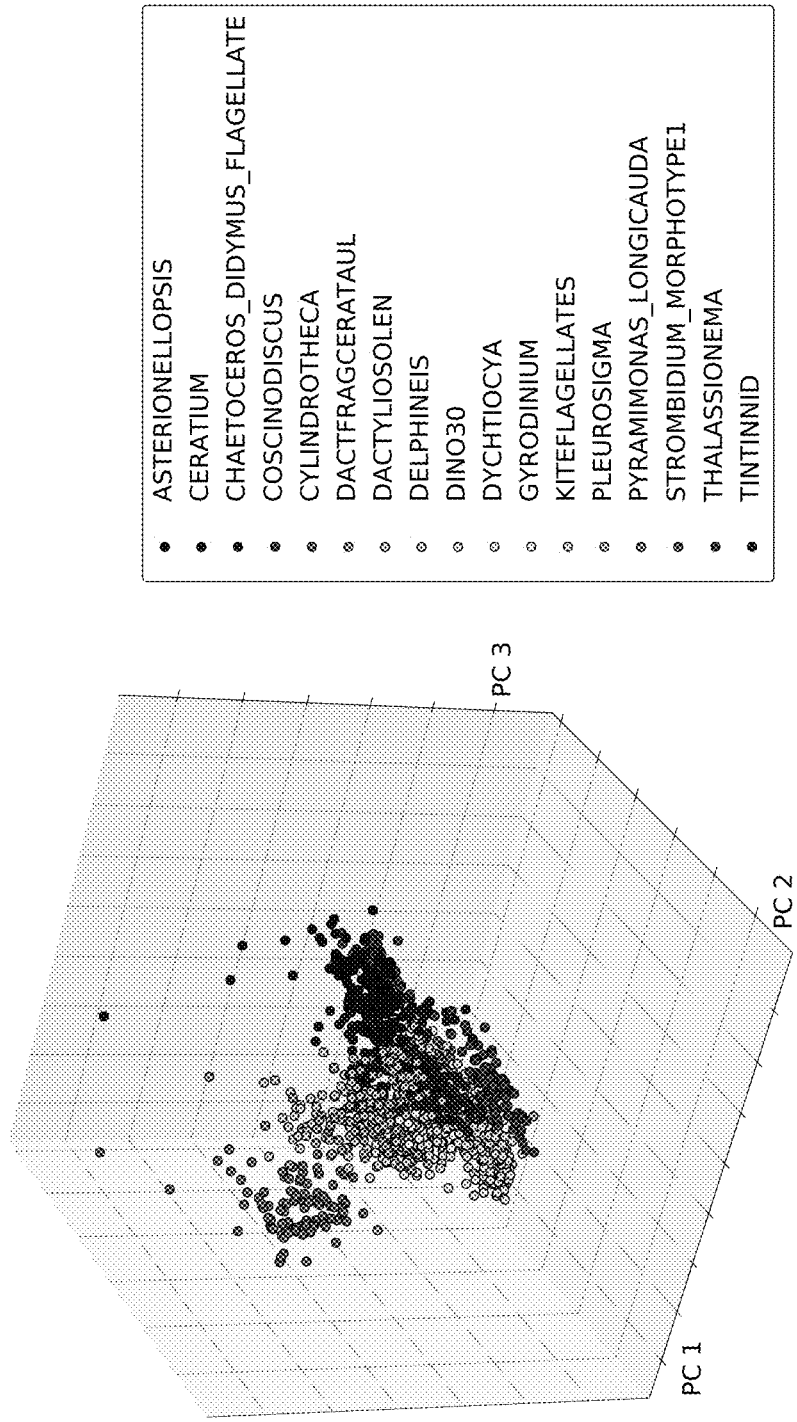
Figure 2D:
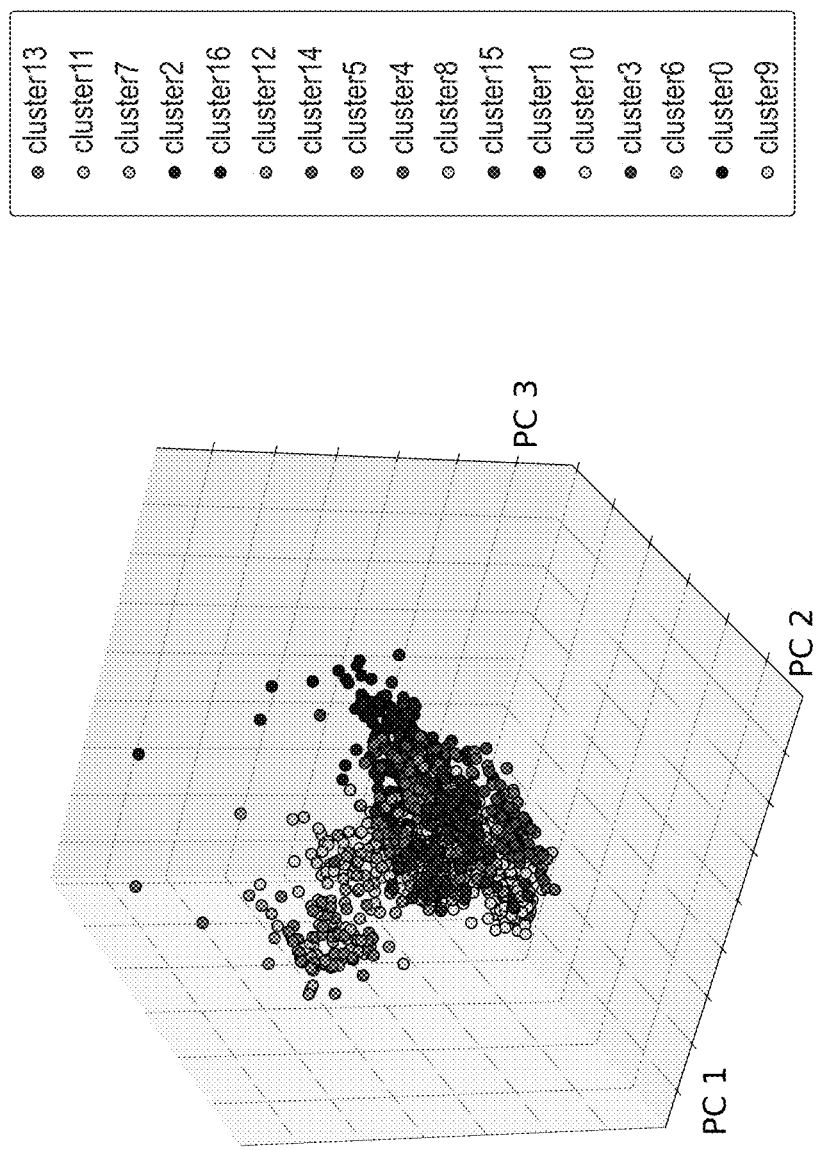
Figure 2E:
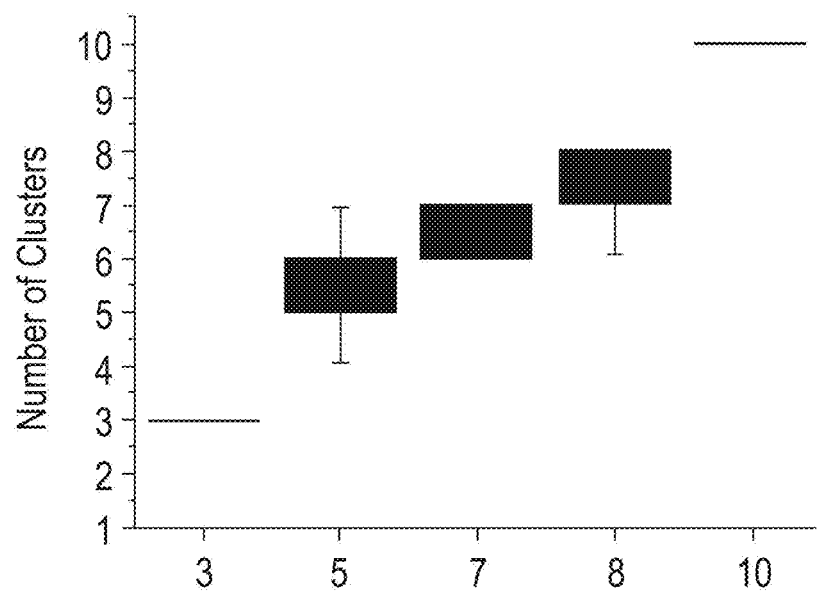
Figure 2F:
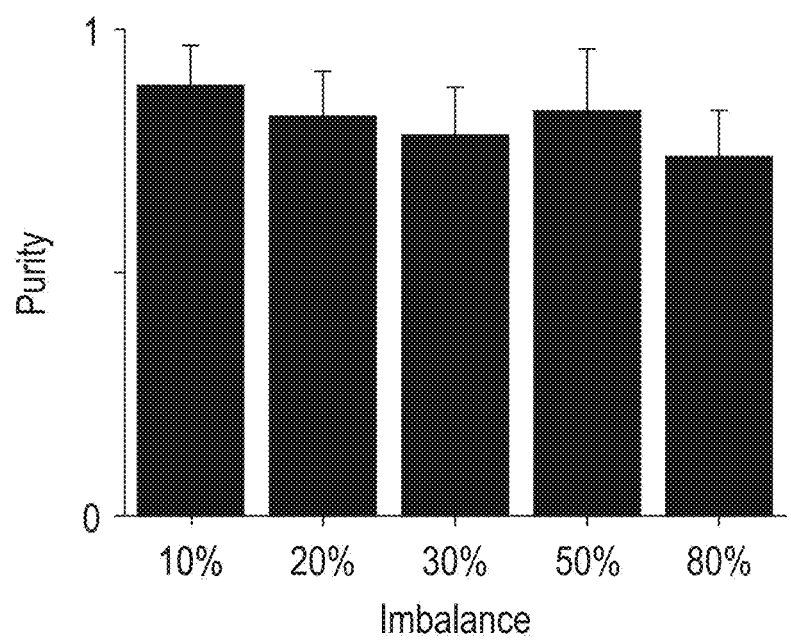
Figure 2H:
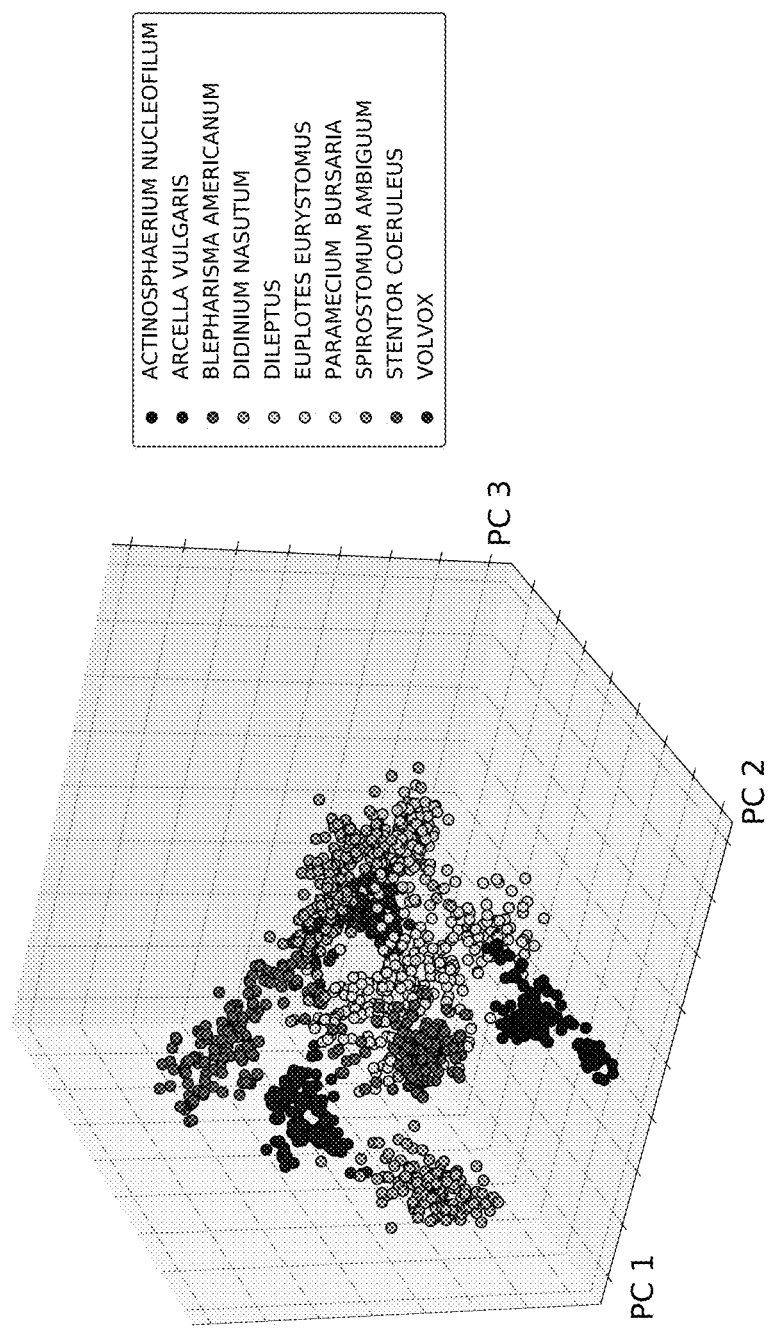
Figure 2I:
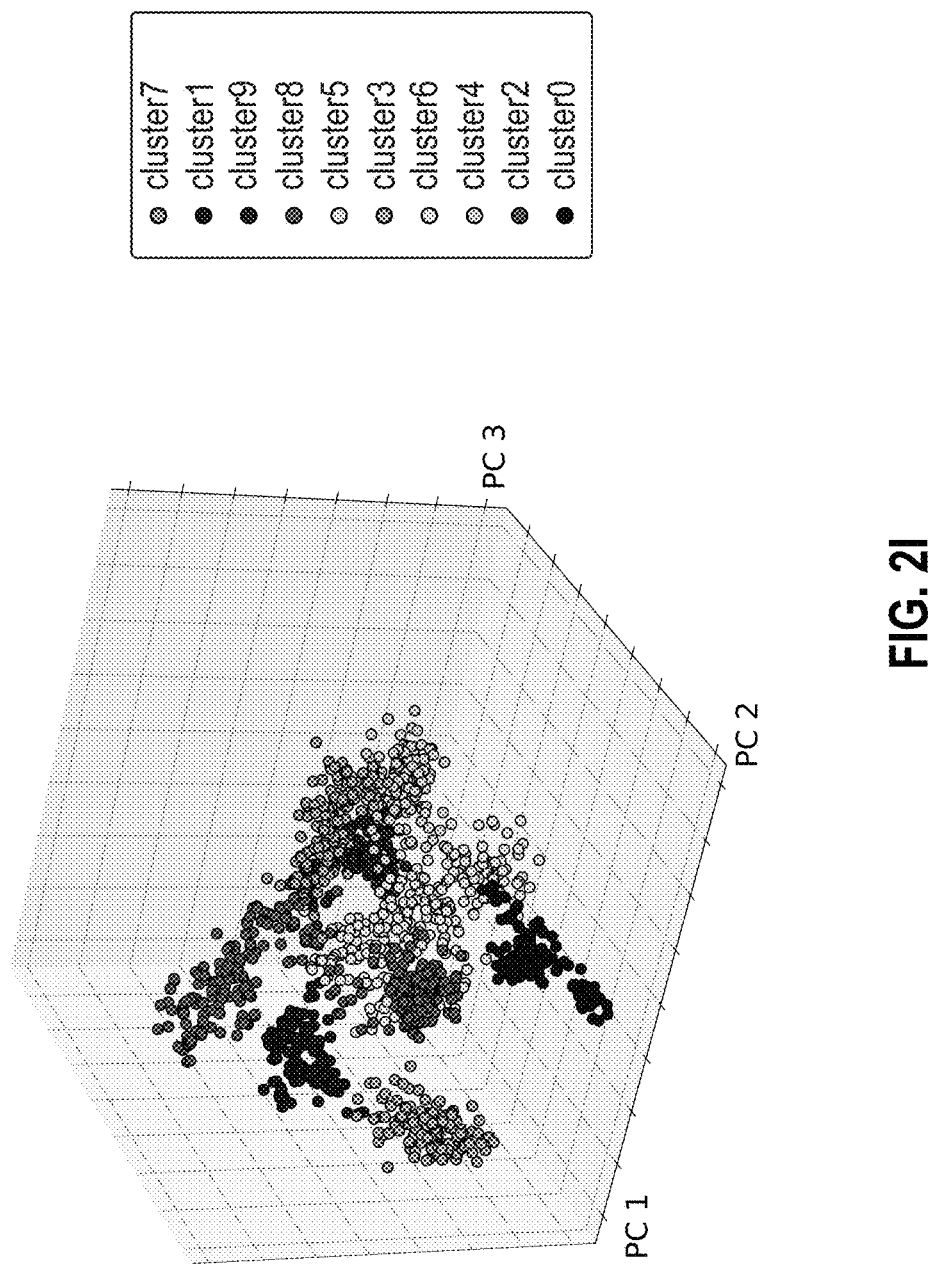

FIG. 2A is a graphical rendering of a PCA (principal component analysis) analysis on the LDM dataset into the features space, and FIG. 2H is a graphical rendering of a PCA analysis on the LDM dataset into the deep features space. In FIGS. 2A and 2H, the first three principal components that account for ~67% of the total variance are plotted, with different colors assigned to the different plankton species. Each species is assigned using ground truth labels. In FIGS. 2B and 2I, the 10 plankton species of FIGS. 2A and 2H, respectively, are assigned to the most overlapping cluster resulting from the unsupervised partitioning procedure. A comparison of FIGS. 2A and 2B and FIGS. 2H and 2I shows both the feature space analysis and the deep features space analysis provide accurate clustering of the plankton species, but that the deep features space analysis has a higher degree of accuracy than the features space analysis.

In FIGS. 2C and 2D, the features space PCA analysis of FIG. 2A and the overlapping cluster procedure of FIG. 2B are applied on the 17-species subset of the WHOI dataset. FIG. 2C represents the PCA space corresponding to the WHOI dataset ground truth labels, and FIG. 2D represents the corresponding PCA space resulting from the unsupervised partition algorithm. The clustering differences seen between FIGS. 2C and 2D highlight the ability of the unsupervised partitioning module of the classifier to distinguish between inter-species plankton morphology. To obtain the data in FIGS. 2C and 2D, a random forest algorithm was trained using the labels provided by the unsupervised partitioning with a train-test ratio of 80:20 resulting in a classification accuracy of ~63%. For comparison, a supervised random forest algorithm was trained using the ground truth labels on the extracted features resulting in a classification accuracy of ~79%.

Clustering accuracy is evaluated using a purity algorithm. The purity algorithm used herein is represented by Formula (2):

$$\text{purity} = \frac{1}{N}\sum_{k}\max_{j}|w_k \cap c_j|, \quad (2)$$

where the class k is associated with the cluster j having the highest number of occurrences, N is the total number of clustering samples, $w=[w_1, w_2, \ldots, w_K]$ indicates the computed set of clusters, and $c=[c_1, c_2, \ldots, c_j]$ corresponds to the set of ground truth classes. A purity value of one corresponds to clusters that perfectly overlap the ground truth. Purity decreases when samples belonging to the same class are split between different clusters, or when two or more clusters overlap with the same species. The purity algorithm is capable of checking for occurrences and automatically adapting to the correct number of non-overlapping clusters.

FIG. 2E is a box plot showing the distribution of number of clusters computed using the PE algorithm for a random subset of species in the LDM dataset (the y-axis representing the different number of species in the LDM dataset). Using the purity algorithm on the clustering data of FIGS. 2B (for the 10 species LDM dataset) and 2D (for the 17 species subset of the WHOI dataset), the performance of three clustering algorithms were compared: k-Means, Fuzzy k-Means, and Gaussian Mixture Model (GMM). The Fuzzy k-Means algorithm reached a purity value of 0.934 for the 10-species LDM dataset outperforming the standard k-Means (purity value=0.887) and GMM (purity value=0.886). A posterior analysis of the results of the GMM showed that this algorithm was not able to distinguish between *Blepharisma americanum* and *Paramecium busaraia*, due to their nearly identical appearance in the acquired videos. While the fuzzy algorithm worked best on the LDM and WHOI plankton datasets, it is to be understood that with other microorganisms, crisp algorithms, such as k-Means or GMM, may also be used. With the plankton datasets, the Fuzzy k-Means algorithm was able to match the fuzziness exhibited by the plankton classes in parameter space explaining the lower accuracy of the crisp algorithms. Based on the foregoing results, the Fuzzy k-Means was used for the unsupervised classifier as is shown in FIG. 1. For the normalized WHOI dataset, the 40 WHOI species selected (Example 1) had an overall purity value of 0.715 with the Fuzzy k-Means algorithm.

As class imbalance can influence the performance of any clustering algorithm, the LDM dataset was tested for class imbalance. FIG. 2F is a bar graph showing the class imbalance versus purity for the LDM dataset. For each of the 10 species in the LDM dataset, a class imbalance was simulated by increasing the number of images available to the Fuzzy k-Means clustering algorithm for the considered species. A test dataset was built where the number of images of one species was set as a fraction between 10% and 80% of the number of images of the other species. Test datasets were prepared for all 10 species. Application of the clustering algorithm to the test datasets consistently inferred the correct number of species, without any overlap, with a minimum average purity value of 0.74±0.09 (corresponding to 80% of class imbalance) and a maximum average purity value equal to 0.90±0.08 (corresponding to 10% of class imbalance), with a maximum purity value of 0.972. The results of the class imbalance test demonstrated that the unsupervised partitioning module of the classifier can accurately cluster data even in the case of strong class imbalance.

Supervised Classification.

At the supervised classification module of the classifier, test samples have been assigned labels that have no correspondence to the actual plankton classes. To classify the labeled test samples, a supervisor classifier must be trained. Three exemplary, but non-limiting, supervisor classifiers are an ANN, a CNN, and an RF algorithm. Within the context of the classifier, the ANN architecture consists of a collection of classifier algorithms, each trained to detect one plankton class. Example 3 and FIG. 6 describe the development of the ANN algorithm for the LDM dataset. In a situation where partial training data are available, a CNN may be used to augment the extracted features. Example 4 and FIG. 7 describe application of a CNN to a deficient plankton training set from the WHOI dataset.

The supervisor classifier may be trained with the clusters provided by the algorithms used in the unsupervised partitioning module as labels. Such procedure includes adopting the result of PE algorithm as an estimation of the number of classes and any of the clustering algorithms (e.g., the k-Means, the Fuzzy k-Means, and/or the GMM algorithm). Using the clusters provided by the trained Fuzzy k-means algorithm, a supervised neural network had a testing accuracy around 95%.

Figure 3A:
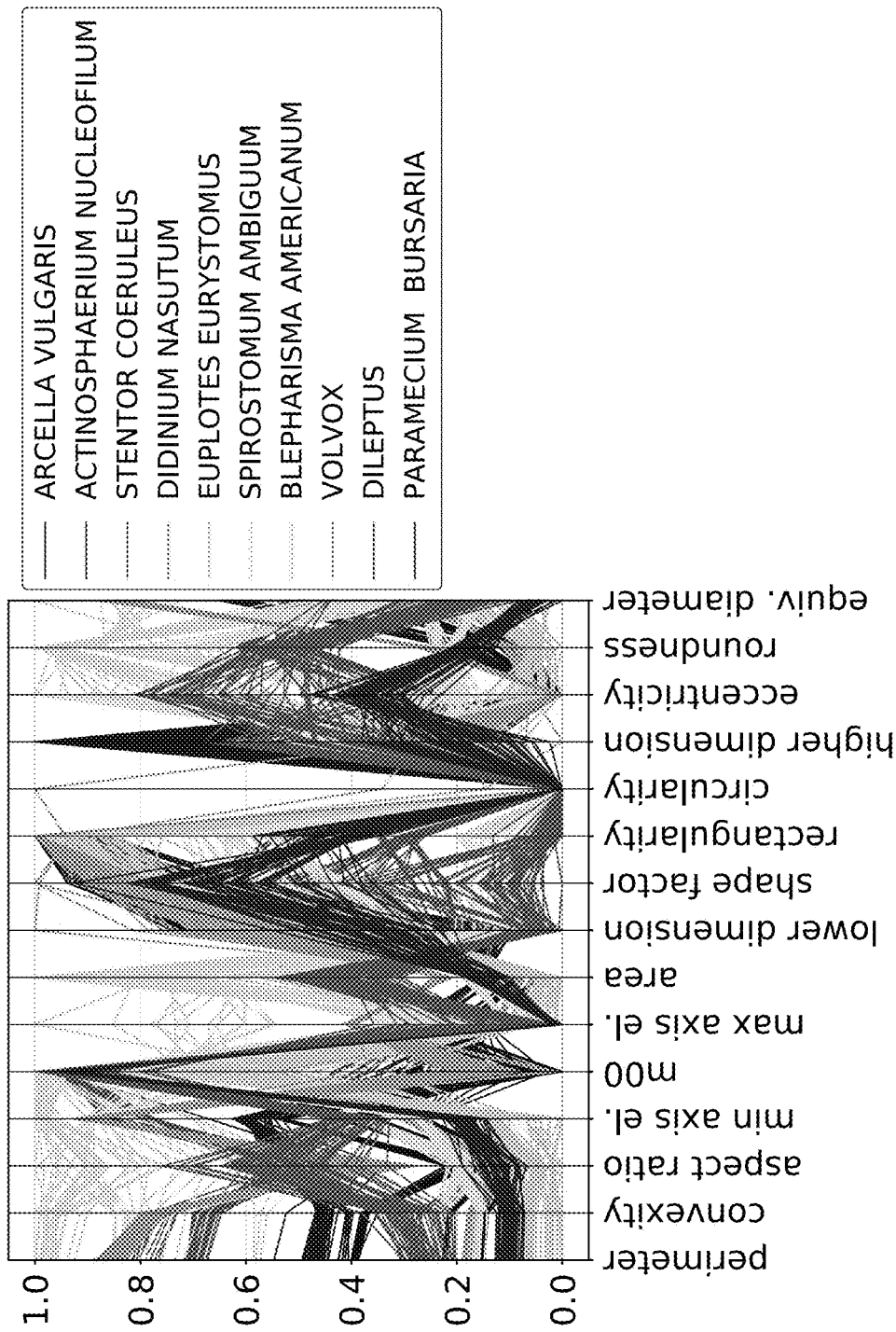
FIGS. 3A-3D are classification plots for the LDM dataset.
Figure 3B:
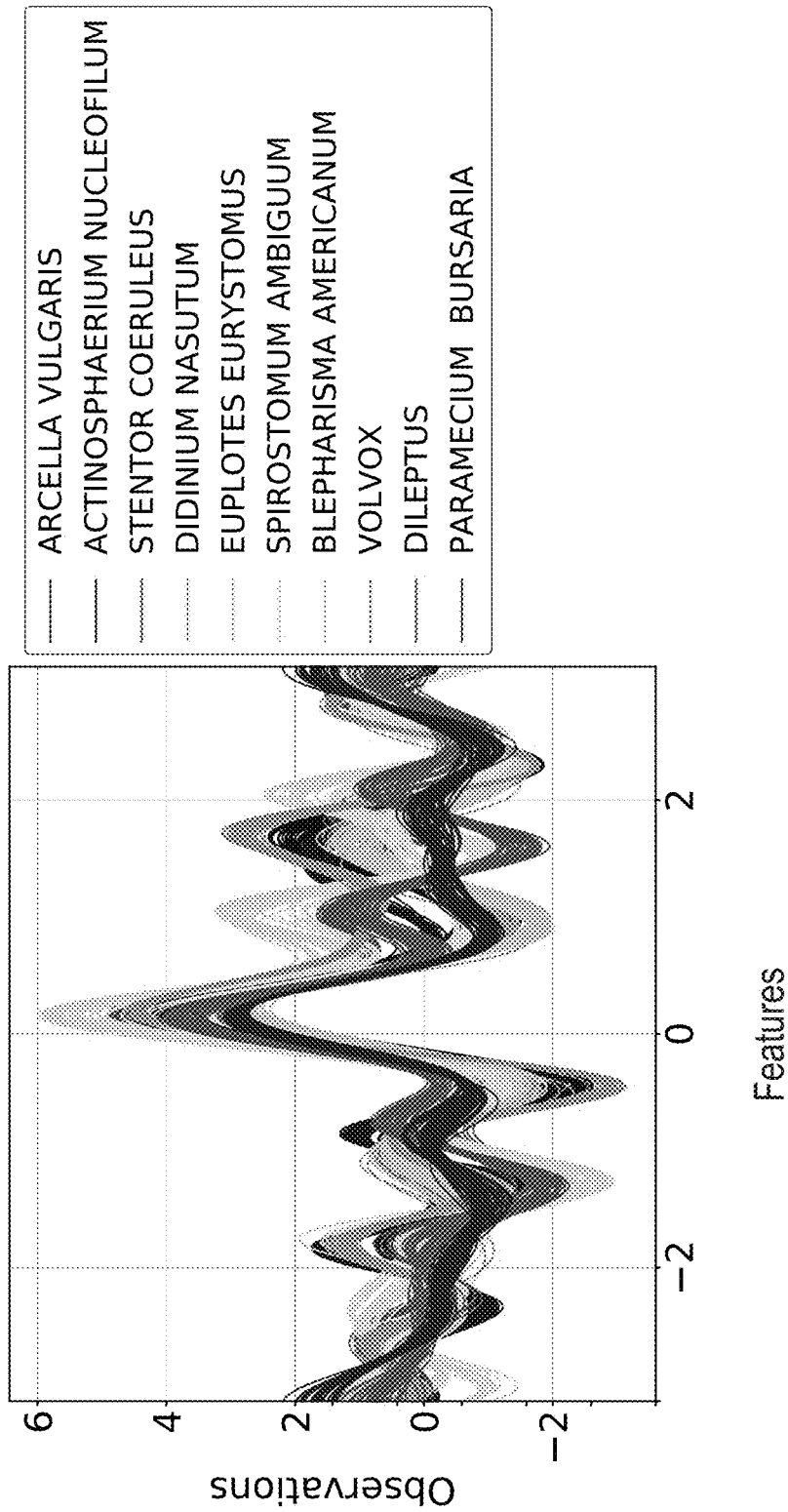
Figure 3C:
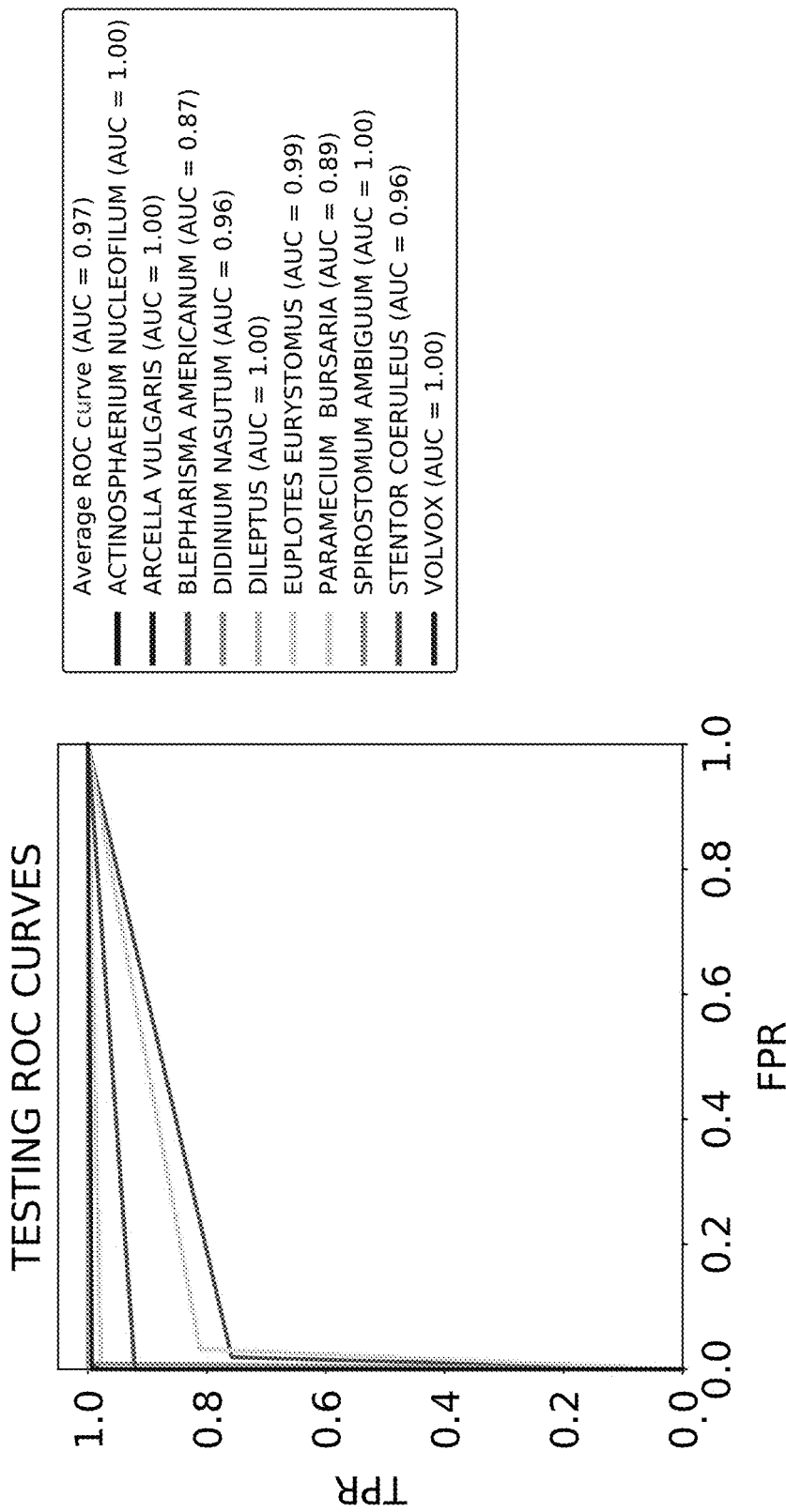
Figure 3D:
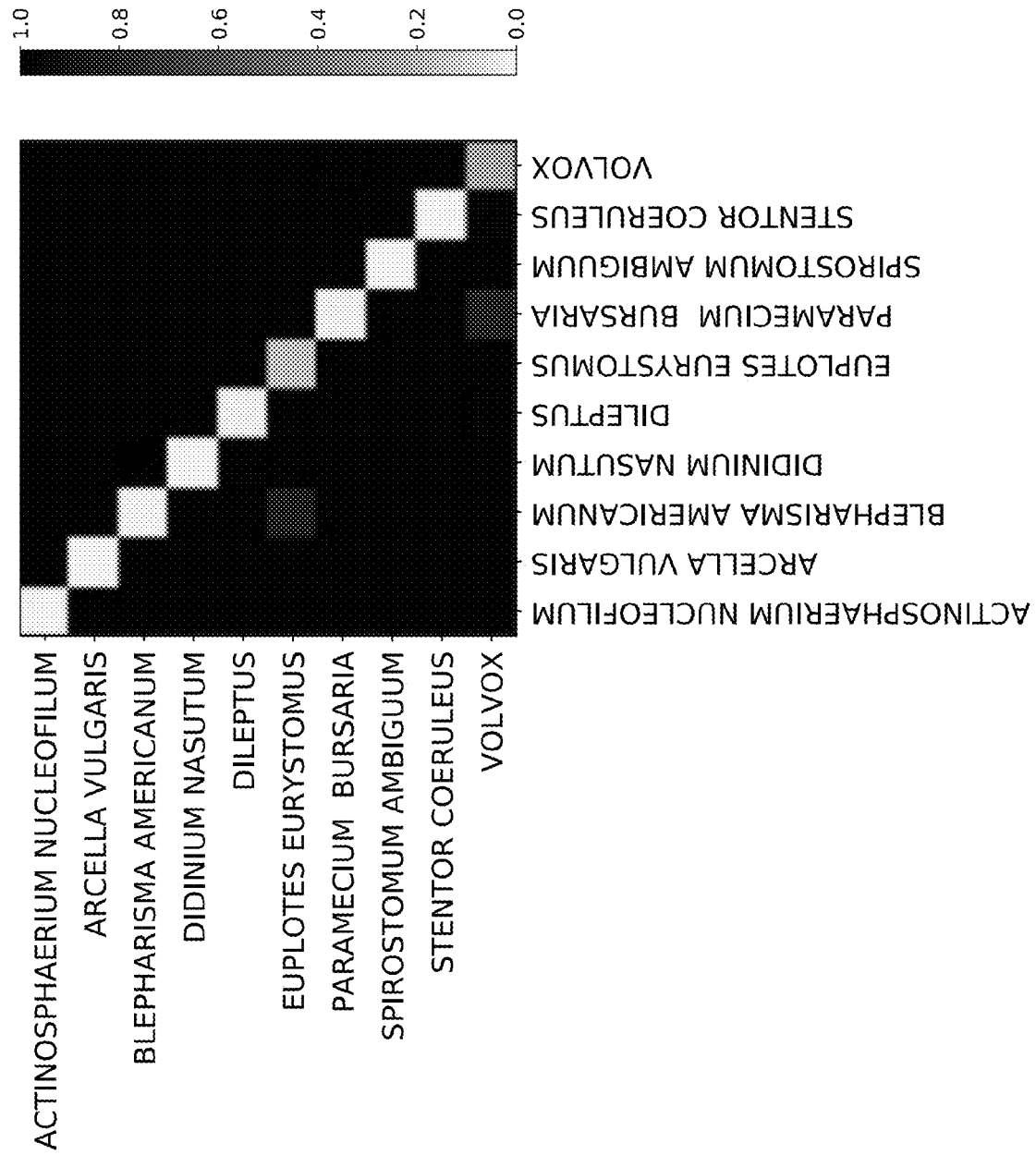

FIGS. 3A-3D are classification data plots for the ANN classifier after training on the labels provided by the Fuzzy k-means clustering algorithm. As shown in FIGS. 3A-3D, the ANN had a classification accuracy of 95% for the LDM dataset. FIGS. 3A and 3B provide multidimensional visualizations of the 10 plankton species of the LDM dataset and demonstrate the discriminating power of the geometrical features in the classification of the plankton species. FIG. 3A are Andrews curves (structure visualization in high-dimensional data) and FIG. 3B are parallel coordinate curves (high-dimensional geometry visualized with parallel lines). FIG. 3C is an ROC (receiver operating characteristic) curve, which plots the true positive rate (TPR) against the false positive rate (FPR) for the ANN classifier. The ROC curves are close to a perfect classifier as evidenced by the testing curves for all species at the top of the TPR curve between 0.8 and 1.0 and at the bottom of the FPR curve at or very near to 0.0. FIG. 3D is a confusion matrix, which is a table that visualizes algorithm performance for a classification model. The confusion matrix is almost diagonal with minor overlap in morphology features between two pairs of plankton species: *Blepharisma americanum* and *Paramecium bursaria*; and *Spirostomum ambiguum* and *Stentor coerouleus*. The misclassification of these species is primarily due to the similarity in the morphology (e.g., shape, size, texture, and structure) of the two pairs of species, influencing the unsupervised training clustering and the subsequent testing of the supervised classifier.

When the RF algorithm was trained using the labels provided by the unsupervised classifier, the RF algorithm had an accuracy of 94%. By contrast, when the same RF algorithm was trained using the actual labels (ground truth) of the training set, the RF algorithm reached an accuracy of around 98%. The close difference in accuracy of the RF algorithm with the two training methods shows that the unsupervised classification approach performs comparably to the correspondent supervised approach for the trained classifier. Since the ANN performed slightly better (99% accuracy) than the RF classifier (98% accuracy), the ANN was used to test the supervised classification module for anomaly and unknown plankton species in test samples.

Anomaly Detection.

For a given class, a sample is considered an anomaly if the sample features are significantly different from the feature average for the class. The DEC described herein adds to the neural network-based supervised classification module with an additional classifier that identifies and classifies unknown species and/or known species with anomalies. Example 5 and FIG. 8 describe application of the DEC detector for plankton species anomaly testing.

Figure 4B:
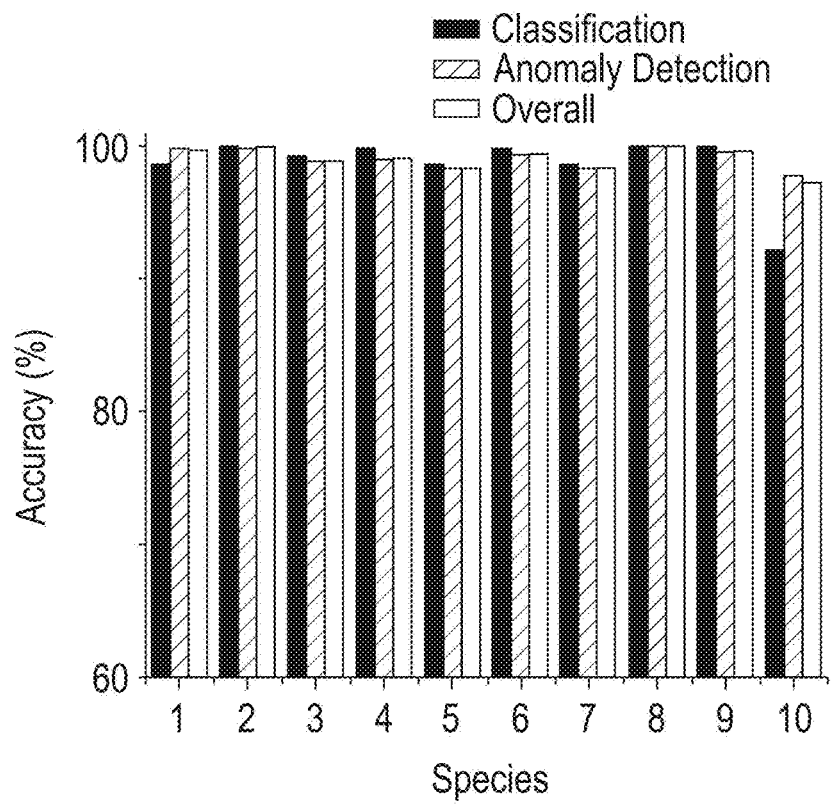

FIGS. 4A-4B show DEC classification and anomaly detection accuracy on plankton data. For each plankton species, one DEC must be trained; thus, for the 10-species LDM dataset, 10 DECs were trained. To test the performance of each of the trained DECs, the plankton samples belonging to the training class were used to test in-class accuracy while the remaining nine species samples were used to test the DEC anomaly detection accuracy. As shown in the confusion matrices of FIG. 4A, the 10 DECs were able to discriminate between the corresponding training species (identified as "In Class" in FIG. 4A) and the remaining nine species (identified as "Anomaly" in FIG. 4A) with high accuracy. The confusion matrix of FIG. 4A is a classic confusion matrix table with a true positive at the upper left (the prediction of the training species is correct), a false positive at the upper right (the prediction of the training species is incorrect), a false negative at the lower left (the prediction of the surrogate species is incorrect), and a true negative at the lower left (the prediction of the surrogate species is correct). FIG. 4B (the numbers on the x-axis correspond to the confusion matrix panel numbers in FIG. 4A) is a bar graph showing an average in-class testing accuracy of 98.8%±2.4%; an average anomaly detection testing accuracy of 99.2%±0.7%; and an average overall testing accuracy for all data of 99.1%±0.9%.

Figure 4C:
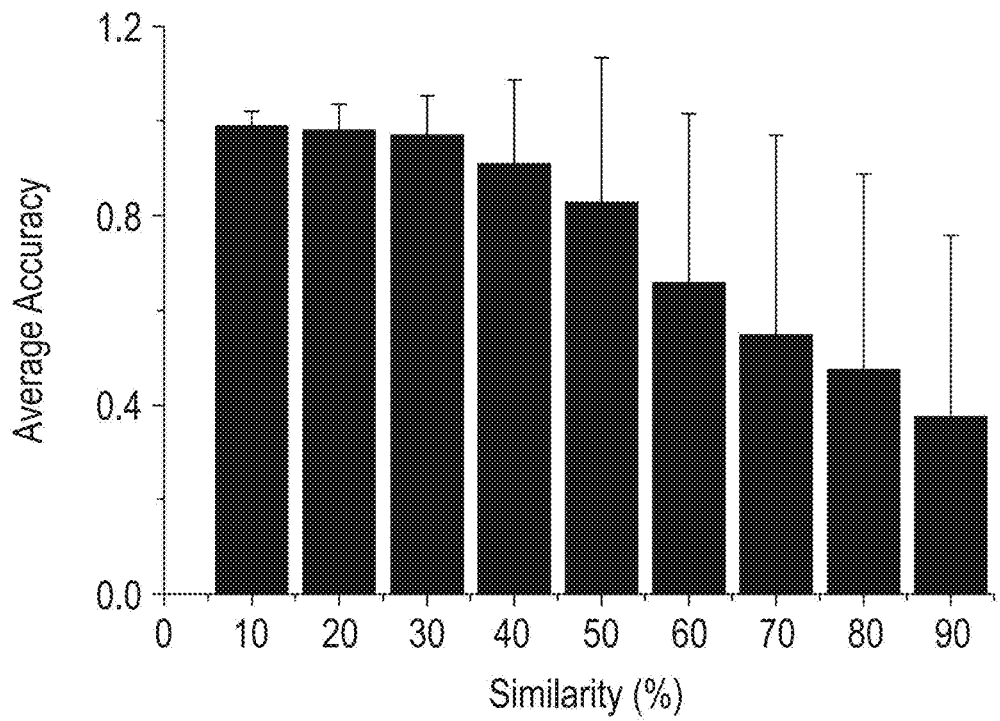
Figure 4D:
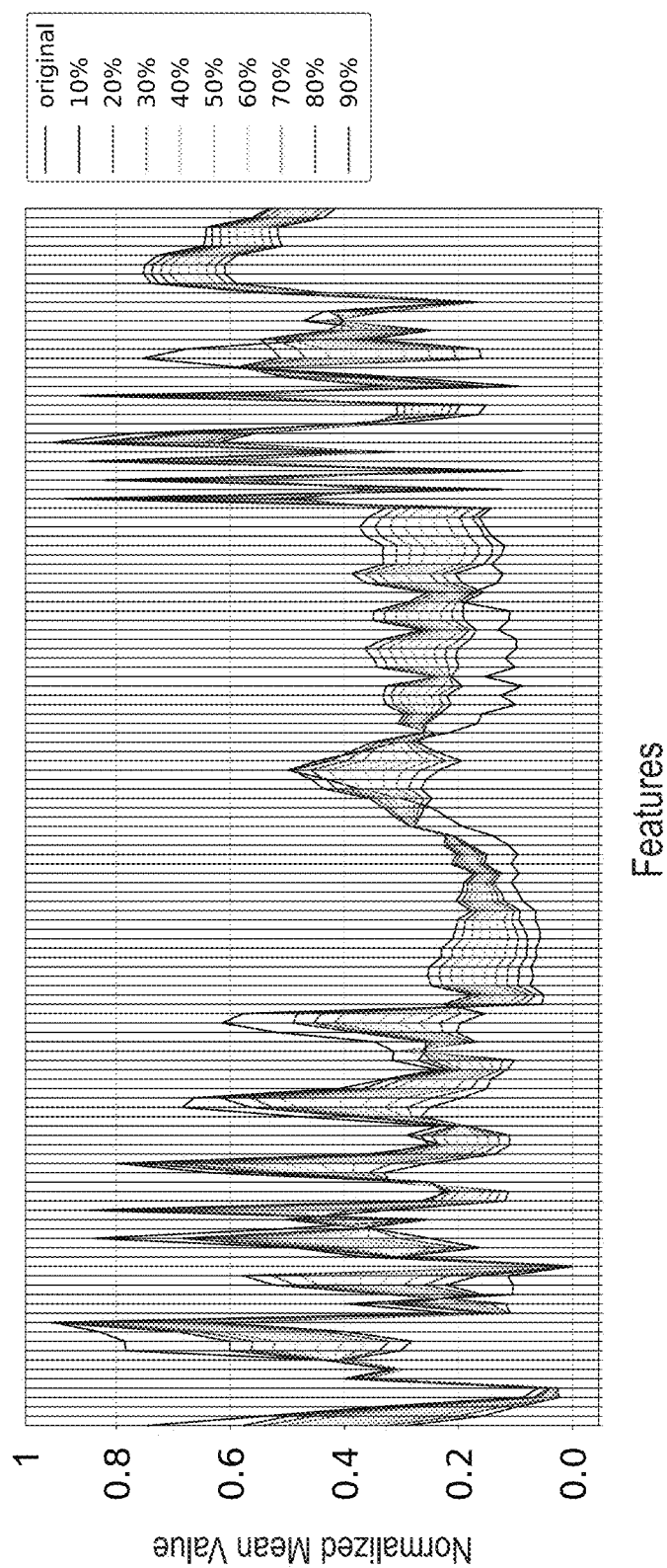

For the anomaly testing, a dataset of nine surrogate plankton organisms was produced (the "surrogate species"), with each of the nine surrogate species having similarities to the LDM dataset species from which the DECs were trained in percentages ranging from 10% to 90% (the "training species"). Example 6 describes the production of the surrogate species. FIG. 4C is a bar graph showing the DEC testing accuracy for varying percentage values of similarity between the surrogate species and the training species. The data from FIG. 4C show that by increasing the similarity between the surrogate species and the training species, the surrogate species approach the features of the training species, resulting in an increase in the average anomaly misclassification rate and a decrease in the overall accuracy levels. Where the similarity between the surrogate species and the training species is up to 30%, the DEC can recognize anomaly species with an average accuracy higher than 98.3%±10.1%. The DEC can maintain an average accuracy of over 82.6% if the species similarity is up to 50%. The accuracy of anomaly detection decreases if the species similarity is over 50%. FIG. 4D is a multidimensional parallel coordinates plot of the resulting distributions for the surrogate species trained with *Spirostomum ambiguum*.

Unknown Species Detection.

Figure 4E:
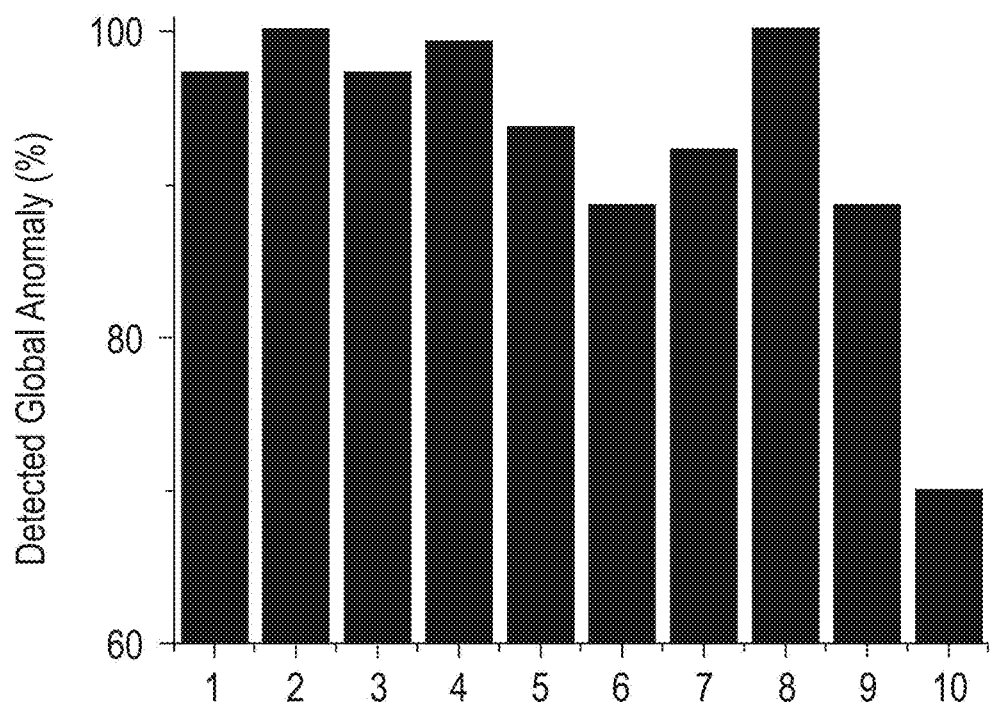

As described herein, the neural networks of the DEC detector are capable of classifying a sample as either a training species (e.g., the plankton species used to train the DEC detector) or as an anomaly (e.g., a sample deviating from the training set projected in the features space). If a sample is left unidentified by all the implemented detectors, it likely represents a sample belonging to an unknown species. Example 7 and FIG. 4E describe the use of the 10 DEC detectors to identify an unknown plankton species. FIG. 4E (the numbers on the x-axis correspond to the confusion matrix panel numbers in FIG. 4A) is a bar graph showing the percentage of global anomaly (i.e., samples detected as anomaly by all of the DECs) when one training species was removed from the 10-species LDM training dataset. For the test, one of the 10 DEC detectors for the LDM training set was removed and the complete 10-species LDM test samples were used as input for the remaining nine DEC detectors (Example 7). The percentages in FIG. 4E reflect the level of accuracy of the nine DEC detectors in detecting unknown species. The average percentage rate of detection was calculated to be 98.3%±10.1%.

Where an unidentified sample is two or more unknown species, a human expert can set a label for the new species so that the DEC detector can be trained for each of the new species. Alternatively, the samples corresponding to the unknown species may be clustered and classified by the unsupervised partitioning step of the classifier, reducing the number of new species to be examined by the human expert.

Real-Time Environmental Monitoring.

Figure 5:
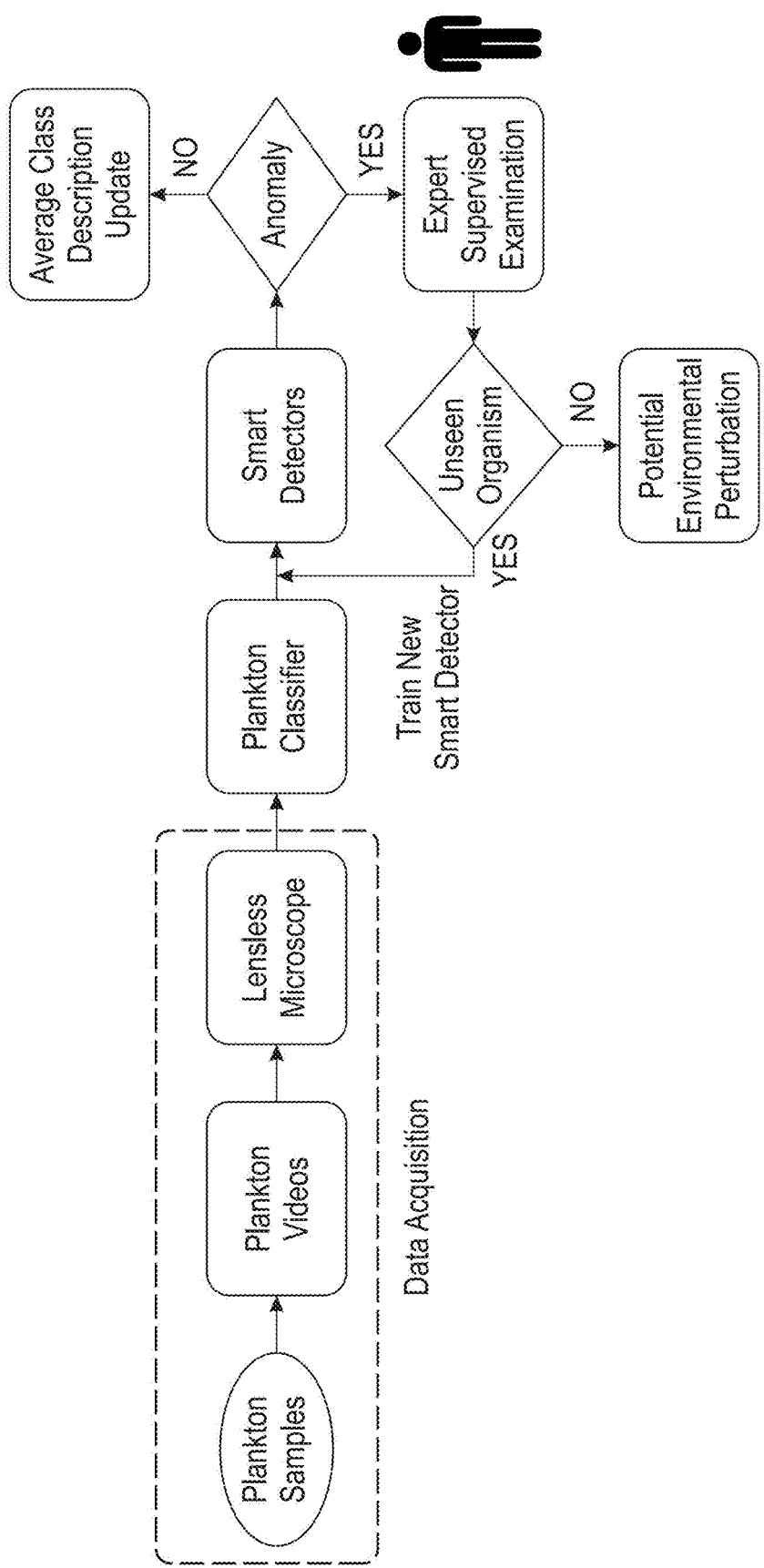
FIG. 5 is a schematic of the classifier for real-time plankton and environmental monitoring.

FIG. 5 is a schematic flowchart of the classifier as a continuous environmental monitoring system. Once the descriptors have been extracted from the acquired videos, they may be used to build a set of DEC detectors. The use of neural network algorithms in the DEC detectors can infer non-linear relationships between features (input) and correlate them with the class description (output) without making any assumptions on the underlying learning model; thus, the plankton classification will depend only on the extracted features. As shown in FIG. 5, if the classifier identifies a plankton species belonging to a specific class, the average set of morphological features is updated, thereby further qualifying the class morphology phase space. If an anomaly is detected, the sample may be sent to an expert for a supervised examination. The expert will determine whether the sample could be a species not represented in the training set (an unknown species), or if the sample belongs to an existing training class, but the sample has morphological features that deviate significantly from the average features space of the corresponding class (an anomaly). If the sample is an unknown species, a new DEC detector will be trained, thus expanding the training sets. The existing and new training sets will be reentered into the aquatic environment in order to provide continuous monitoring of the aquatic environment. As new unknown species are found, additional DECs will be trained and reentered into the environment. In the case of an anomaly, the identified anomalies may represent local environmental perturbations, either natural or man-made. With anomalies, the existing DECs may be retrained to update the algorithm (rather than training new DECs in the case of unknown species).

The neural network-based classifier described herein is a small-sized, low-powered, portable device that may be used for image capture, image processing, classification of known microorganisms, and detection and classification of unknown microorganisms and known microorganisms with anomalies. The classifier may be further coupled to a local (e.g., laptop, server) or cloud-based system for implementation of the algorithm training required for the unsupervised partition and supervised classifier modules of the classifier. Within the context of aquatic microorganism (such as plankton) detection and classification, the classifier may be placed in the water for real time continuous smart environmental monitoring systems to monitor the microorganisms and by extension, the entire aquatic ecosystem.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

Example 1

Plankton Videos and Image Processing (LDM and WHOI Datasets)

Color videos (1920×1080) of 10 plankton species were taken with an LDM (lensless digital microscope) for 10 seconds, captured at 30 frames per second. Background subtraction was applied to each frame to detect the swimming plankton in the image. A contour detector was applied to the processed image to create a bounding box around each plankter; however, the organisms were still capable of swimming in and out of the field of view (FOV) during acquisition. Only images with fully visible organisms were selected. An algorithm was used to select the fully visible organisms by identifying images where the bounding box touched the borders of the FOV. From the collection of images for the 10-species LDM dataset, a training set of 640 images with 500 training images and 140 testing images was selected for each class. The number of classes was obtained using the PE algorithm described herein.

A set of additional plankton images were obtained from WHOI as a testing benchmark for the plankton classifier. A collection of 40 species of plankton were selected and 100 images were taken for each of the 40 species.

Example 2

Feature Extraction (LDM and WHOI Datasets)

For each plankter image in the LDM dataset, 131 features were extracted from the processed images according to the following morphologies: geometric features, invariant moments (Hu moments and Zernlike moments), texture (image intensity features, Haralick Features, and local binary patterns), and Fourier descriptors (Table 1). The geometric features include area, eccentricity, rectangularity and other morphological descriptors, that have been used to distinguish plankton by shape and size. The invariant Hu and Zernike moments are widely used in shape representation, recognition and reconstruction. Texture based features encode the structural diversity of plankton. Fourier Descriptors (FD) are widely used in shape analysis as they encode both local fine-grained features (high frequency FD) and global shapes (low frequency FD). Table 1 provides the list of the 131 morphological features that were extracted from the processed images for the 10-species LDM dataset.

TABLE 1

| MORPHOLOGY | NUMBER | DESCRIPTION |
| --- | --- | --- |
| Geometric Features | 14 | Area (pixels), Area (0-th order moment), Perimeter, Eccentricity, Rectangularity, Roundness, Shape Factor, Width & Height (minimum fitting rectangle), Circularity, Major & Minor axis (fitting ellipse), Equivalent Diameter, Convexity. |
| Hu Moments | 7 | Hu moments computed from the normalized central image moments. |
| Zernlike Moments | 25 | Zernlike moments up to order 5. |
| Image Intensity Features | 8 | Blue/green channels ratio, red/green channels ratio, red/blue channels ratio, gray levels histogram statistical features (skewness, kurtosis, mean value, standard deviation, entropy). |
| Haralick Features | 13 | The first 13 features computed from the Gray Scale Co-occurrence Matrix (GSCM). |
| Local Binary Patterns | 54 | Local binary patterns summarize the structures of the image comparing each pixel to its neighbor. |
| Fourier Descriptors | 10 | Fourier descriptors are contour-based features invariant with respect to rotation, scaling, and translation. |

Figure 7:
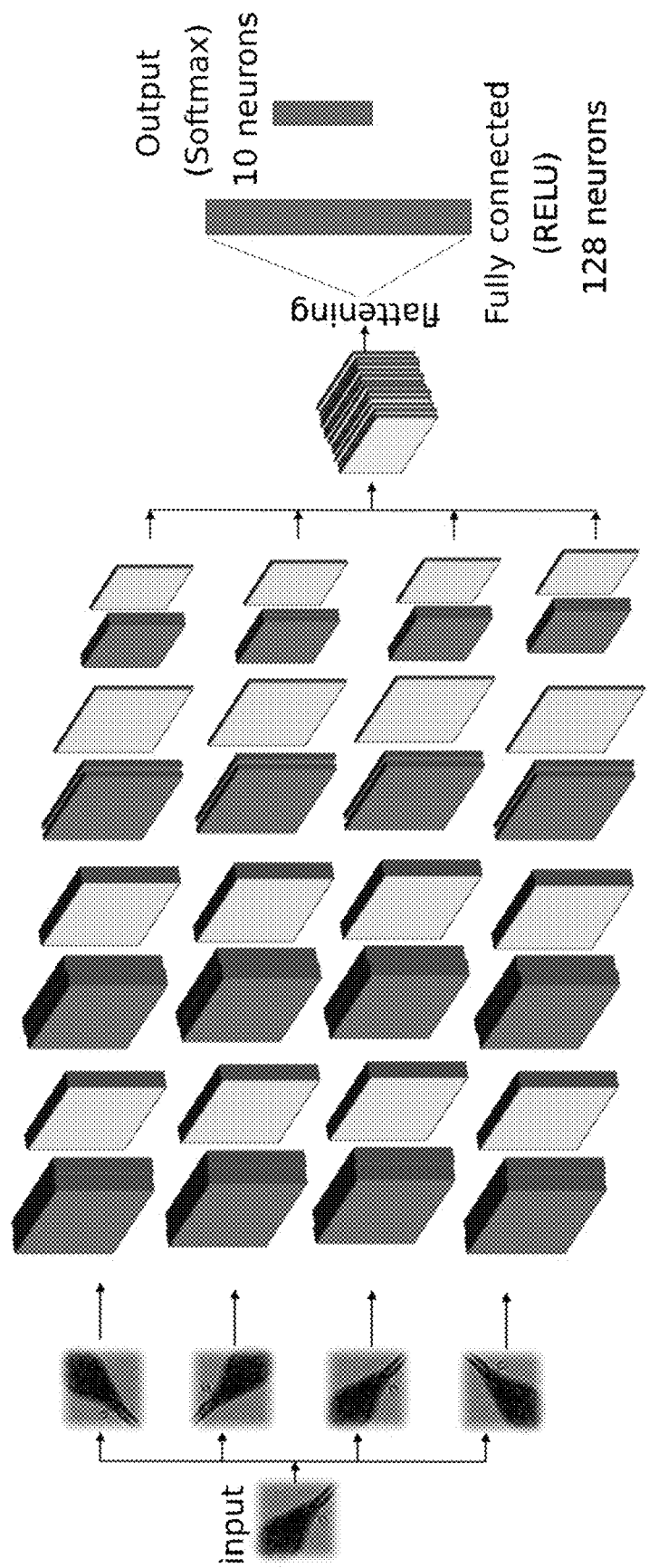
FIG. 7 is a schematic of a convolutional neural network (CNN) architecture implemented for the purpose of deep features extraction from a partial training set.

For the 40-species WHOI dataset, the features set selected was identical to the features set used for the LDM dataset minus three-color features since the LDM microscope is a color-based sensor, while the IFCB (Imaging FlowCytobot) optical imager used by WHOI is monochromatic; thus, the three extracted features from the LDM dataset that were missing from the WHOI dataset were color-based features. With reference to FIG. 7, a set of 128 features from the collection of 40 species (with 100 images per species as described in Example 1) were randomly selected using segmented binary images and gray-scale images containing the plankton body. The WHOI dataset had three less extracted features than the LDM dataset because the LDM microscope is a color-based sensor, while the IFCB optical imager used by WHOI is monochromatic.

Example 3

Artificial Neural Network (ANN) Build for Classification Based on Extracted Features (LDM Dataset)

Figure 6:
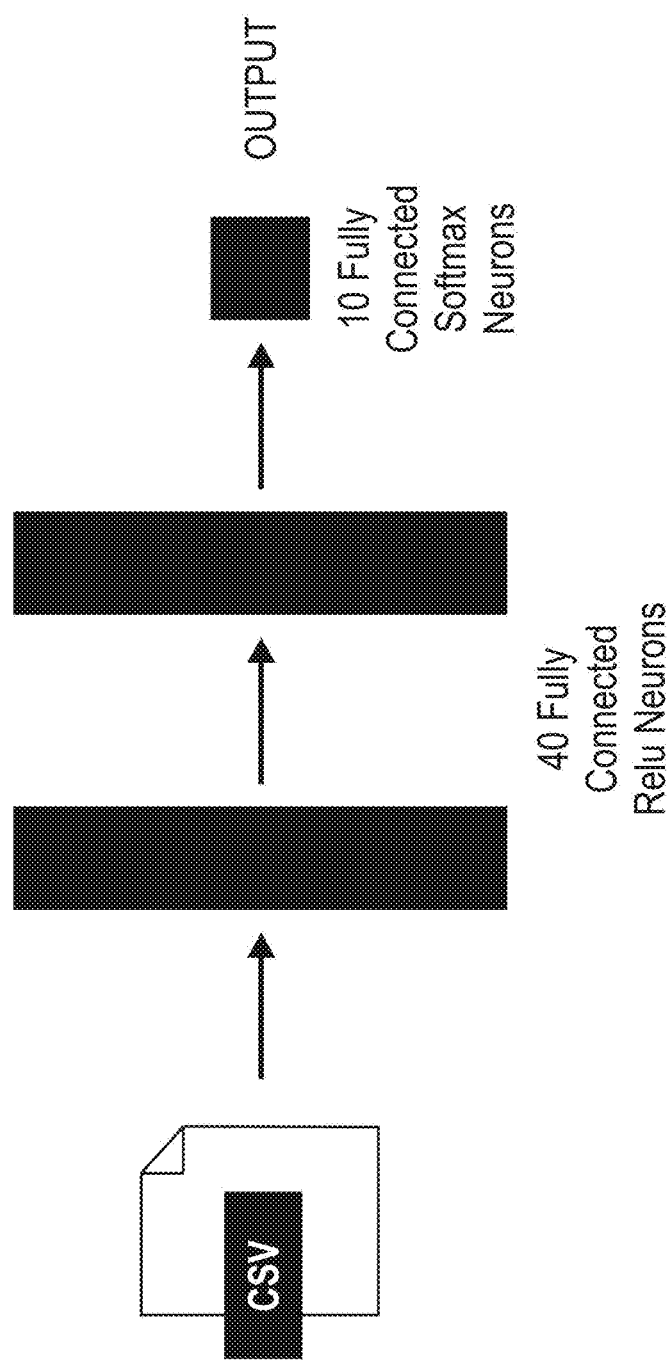
FIG. 6 is a schematic of an artificial neural network (ANN) architecture implemented for classification based on extracted features.

For the LDM dataset, ANNs were used to build a classifier able to predict the species for each extracted image using a shadow microscope. The network used was shallow, with two hidden layers of 40 neurons and an output layer with as many neurons as the number of species to classify. The output layer was made up of k neurons, where k is the number of clusters obtained with the unsupervised partitioning. The developed ANN used a Rectified Linear Unit (ReLU) activation function and dropout to reduce the overfitting from 40 fully connected ReLU neurons to 10 fully connected SOFTMAX® (Molecular Devices Corp., Menlo Park, Calif., USA) neurons (FIG. 6). The network was trained using 200 epochs, root mean square as an optimizer, a learning rate $\lambda=0.005$, and categorical cross-entropy as loss function. The training required 50 seconds on a MAC book PRO, core i7-2.9 gHz, solid state disk and 16 GB of RAM. The neural network was implemented using KERAS (open-source neural-network library written in Python), a powerful high-level neural network application program interface (API) running on top of TENSORFLOW® (Google LLC, Mountain View, Calif., USA).

Example 4

Convolutional Neural Network (CNN) for Deep Features Extraction (WHOI Dataset)

For the WHOI dataset, a CNN using eight convolutional layers and two fully connected layers was implemented (FIG. 7). The CNN architecture was customized to be invariant with respect to rotation. Each input sample was rotated four times at multiples of 90°, and the tensors resulting from the features extraction module were concatenated and used to train the fully connected layers. The neural network was trained for 60 epochs, using stochastic gradient descent with learning rate equal to $10^{-5}$, using data augmentation by means of translation, zooming, and rotation. The implemented rotational invariance module performed a data augmentation operation, which has utility for deep features extraction when partial training data is available. In the CNN schematic of FIG. 7, the blue layers represent convolutional layers and the gray layers represent max pooling 2D operation. The 128 fully connected ReLU neurons represent the features set of the LDM plankton classifier, which the ReLU activation and dropout function reduced to 10 fully connected SOFTMAX neurons.

Example 5

Application of the Delta-Enhanced Class (DEC) Detector for Anomaly Testing

Figure 8:
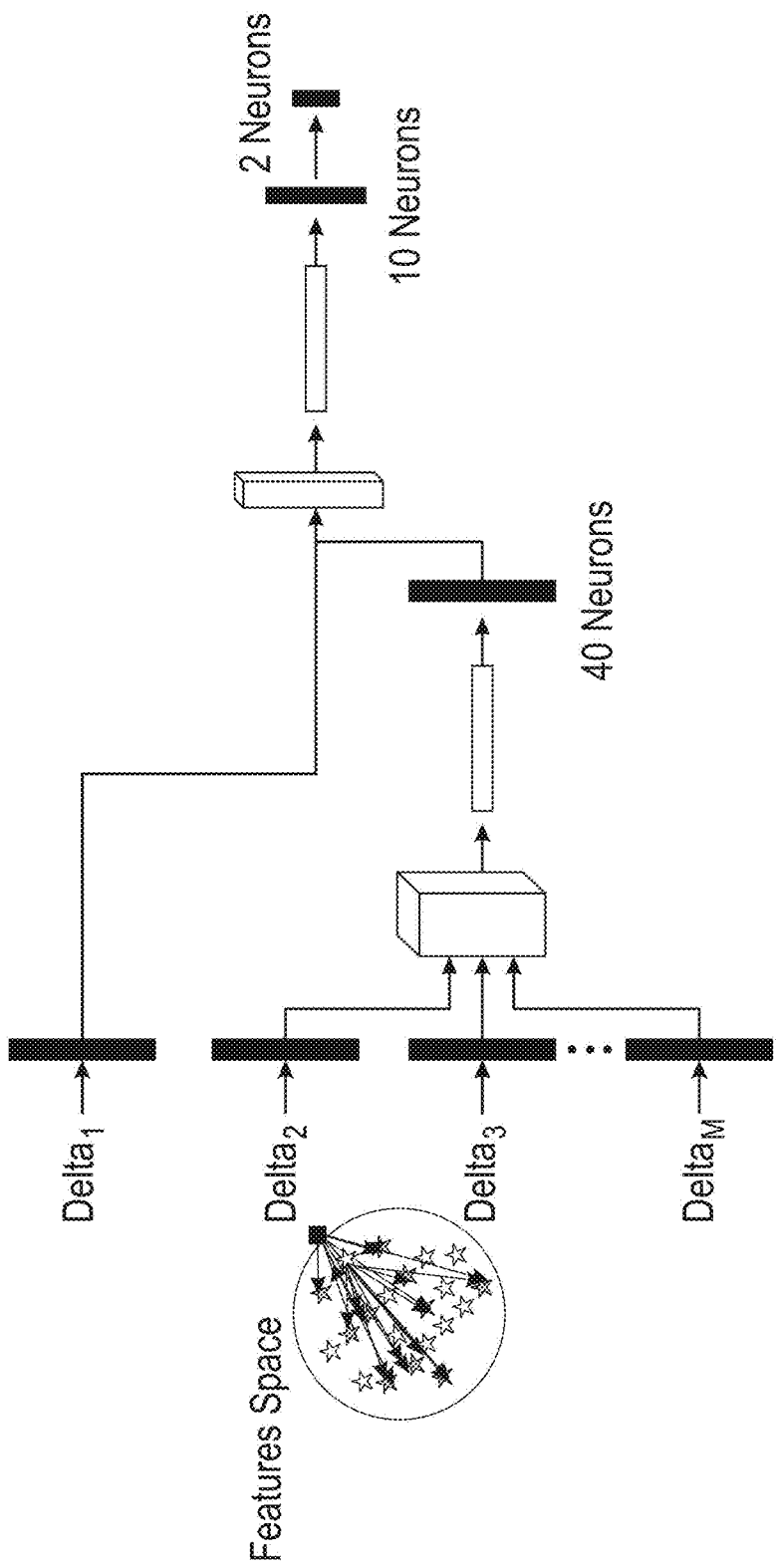
FIG. 8 is a schematic of the DEC architecture described herein.

The deep neural network DEC (Delta-Enhanced Class) detector was tested for anomaly detection. The DEC detector's architecture is represented in FIG. 8, and shows a 2-neuron output, indicating that the sample is either a member of the class or is an anomaly (i.e., not a member of the class). For each observation, the neural network was trained with the actual features vector and a set of randomly selected points from the training class dataset. For each of the selected points, a custom network layer (the delta layer) was defined that computed the difference in absolute value (as a vector, feature by feature) between the actual observation and the extracted random set. The vector of differences and the actual observations were used as inputs to the neural network, which assigned the proper weights to the inputs during training. The set of points to select for the DEC is a hyperparameter that requires tuning. Through testing, 25 points were found to provide the optimal tradeoff accuracy and computational cost.

Values for the actual observations and the difference vectors were inputted into a dense layer of 40 neurons and processed independently (FIG. 8). The outputs corresponding to the differences were then merged, flattened, and again inputted to the 40-neuron dense layer. Finally, the output of the last operation was merged with the observation vectors and used as input to a 10-neuron dense layer. The 2-neuron output corresponded to the in-class and anomaly labels.

Example 6

Production of Surrogate Plankton Species Based on the LDM Dataset

To test the performance of the DEC detector to detect unknown species, an in-silico surrogate plankton data set based on the LDM dataset was produced. Nine different in-silico species with increasing levels of similarity (step size 10%) were generated by taking a feature-by-feature weighted average of the 10 species in the LDM dataset. Starting with a uniform weight distribution, the weight for the plankton species corresponding to the trained DEC detectors for each of the 10 LDM species was increased in steps from 0.1 up to 0.9, obtaining nine different surrogate species.

Example 7

Application of the DEC Detector for Testing for Unknown Plankton Species

The 10 DEC detectors for the LDM dataset were used to test the accuracy of the classifier for identifying an unknown plankton species. From the unsupervised partitioning ensemble described herein, one class was removed and considered as never seen before. The removed samples were tested by the remaining nine DEC detectors. A sample was considered as a global anomaly (i.e., belonging to an unseen species) if all the trained DEC detectors recognized it as an outlier. The number of global anomalies reflected the algorithm accuracy in detecting a new species. The procedure was repeated for the remaining nine plankton classes. The average detection accuracy for the 10 DEC detectors in detecting global anomalies was calculated to be 98.3%±10.1% (FIG. 4E), demonstrating the ability of the classifier to detect the presence of a new species.

We claim:
1. A method comprising:
classifying known species from among a population of microorganisms, wherein each of the known species is classified according to a collection of features extracted from image data;
developing a neural network for each of the known species;
applying each of the neural networks to the population of microorganisms, thereby identifying microorganisms with features that are different from the features of the known species;
identifying (i) known species with anomalies from within the population of microorganisms and (ii) unknown species, based upon the features that are different from the features of each of the known species.
2. The method of claim 1, wherein the collection of features is selected from the group consisting of shape, size, texture, structure, behavior, and combinations thereof.
3. The method of claim 1, wherein the known species are classified with an unsupervised partitioning algorithm.
4. The method of claim 3, wherein the unsupervised partitioning algorithm is selected from the group consisting of a partition entropy algorithm, a purity algorithm, a random forest algorithm, a clustering algorithm, and combinations thereof.
5. The method of claim 4, wherein the clustering algorithm is selected from k-Means, Fuzzy k-Means, Gaussian Mixture Model (GMM), and combinations thereof.
6. The method of claim 3, wherein the neural network is trained with the unsupervised partitioning algorithm.
7. The method of claim 1, wherein the neural network is selected from the group consisting of an artificial neural network, a convolution neural network, a random forest algorithm, and combinations thereof.
8. The method of claim 1, wherein the microorganisms are selected from the group consisting of plankton, flagella, amoeba, paramecia, bacteria, protozoans, eukaryotic organelles, prokaryotic organelles, and combinations thereof.
9. A method comprising:
classifying known plankton species from among a population of different plankton species, wherein each of the known plankton species is classified according to a collection of features extracted from image data;
developing a neural network for each of the known plankton species;

applying each neural network to the population of different plankton species, thereby identifying plankton species with features that are different from the features of the known plankton species; and identifying (i) known plankton species with anomalies from within the population of different plankton species and (ii) unknown plankton species, based upon the features that are different from the features of the known plankton species.

10. The method of claim 9, wherein the collection of features is selected from the group consisting of shape, size, texture, structure, behavior, and combinations thereof.

11. The method of claim 9, wherein the known species are classified with an unsupervised partitioning algorithm.

12. The method of claim 11, wherein the neural network is trained with the unsupervised partitioning algorithm.

13. The method of claim 11, wherein the unsupervised partitioning algorithm is selected from the group consisting of a partition entropy algorithm, a purity algorithm, a random forest algorithm, a clustering algorithm, and combinations thereof.

14. The method of claim 13, wherein the clustering algorithm is selected from k-Means, Fuzzy k-Means, Gaussian Mixture Model (GMM), and combinations thereof.

15. The method of claim 9, wherein the neural network is selected from the group consisting of an artificial neural network, a convolution neural network, a random forest algorithm, and combinations thereof.

* * * * *